United States Patent
Georgeson et al.

(10) Patent No.: US 10,168,287 B2
(45) Date of Patent: Jan. 1, 2019

(54) AUTOMATED DETECTION OF FATIGUE CRACKS AROUND FASTENERS USING MILLIMETER WAVEGUIDE PROBE

(71) Applicant: The Boeing Company, Chicago, IL (US)

(72) Inventors: Gary E. Georgeson, Tacoma, WA (US); Steven K. Brady, Renton, WA (US); Donald D. Palmer, Jr., Ballwin, MO (US)

(73) Assignee: The Boeing Company, Chicago, IL (US)

( * ) Notice: Subject to any disclaimer, the term of this patent is extended or adjusted under 35 U.S.C. 154(b) by 637 days.

(21) Appl. No.: 14/738,359

(22) Filed: Jun. 12, 2015

(65) Prior Publication Data

US 2016/0363543 A1 Dec. 15, 2016

(51) Int. Cl.
- *G01N 22/02* (2006.01)
- *G01S 13/88* (2006.01)
- *G01S 13/86* (2006.01)

(52) U.S. Cl.
CPC .............. *G01N 22/02* (2013.01); *G01S 13/88* (2013.01); *G01S 13/867* (2013.01)

(58) Field of Classification Search
CPC ........ G01N 22/02; G01S 13/88; G01S 13/867
USPC .......................................................... 342/22
See application file for complete search history.

(56) References Cited

U.S. PATENT DOCUMENTS

| | | | |
|---|---|---|---|
| 4,864,260 A | 9/1989 | Huard | |
| 6,274,279 B1 | 8/2001 | Hampp et al. | |
| 6,545,469 B1 | 4/2003 | Batzinger et al. | |
| 7,301,335 B2 * | 11/2007 | Sun | G01N 27/82 324/232 |
| 7,352,176 B1 | 4/2008 | Roach et al. | |
| 7,626,383 B1 | 12/2009 | Sun et al. | |
| 8,274,279 B2 | 9/2012 | Gies | |
| 8,701,276 B2 * | 4/2014 | Burke | H01L 21/67144 29/739 |
| 8,981,771 B2 | 3/2015 | Thompson et al. | |

(Continued)

OTHER PUBLICATIONS

Zoughi et al., "Microwave and millimetre wave sensors for crack detection", Fatigue & Fracture Engineering Materials & Structures, vol. 31, No. 8 (2008), pp. 695-713.

(Continued)

*Primary Examiner* — Frank J McGue
(74) *Attorney, Agent, or Firm* — Ostrager Chong Flaherty Flaherty & Broitman P.C.

(57) ABSTRACT

An automated high-speed method for inspecting metal around fasteners and a computer-controlled apparatus for performing that inspection method. The apparatus comprises a multi-motion inspection head mounted on a scanning bridge, a robotic arm, or a robotic crawler vehicle. The multi-motion inspection head comprises a millimeter waveguide probe and a motorized multi-stage probe placement head that is operable for displacing the waveguide probe along X, Y and Z axes to achieve multiple sequenced motions. The waveguide probe is attached to a mandrel that is rotatably coupled to an X-axis (or Y-axis) stage for rotation about the Z axis. Smart servo or stepper motors with feedback control are used to move the waveguide probe into place and then scan across or around a fastener head to inspect for cracks that may be under paint.

7 Claims, 12 Drawing Sheets

(56) References Cited

U.S. PATENT DOCUMENTS

| | | | |
|---|---|---|---|
| 2007/0046525 A1* | 3/2007 | Holbrook | G01S 13/89 342/22 |
| 2007/0069720 A1 | 3/2007 | Goldfine et al. | |
| 2009/0302835 A1 | 12/2009 | Sun et al. | |
| 2012/0306482 A1* | 12/2012 | Thompson | G01N 22/02 324/238 |
| 2017/0082552 A1* | 3/2017 | Kim | G02B 27/0988 |

OTHER PUBLICATIONS

Ghasr et al., "Millimeter—Wave Differential Probe for Nondestructive Detection of Corrosion Precursor Pitting", IEEE Transactions on Instrumentation and Measurement, vol. 55, No. 5 (Oct. 2006), pp. 1620-1627.

* cited by examiner

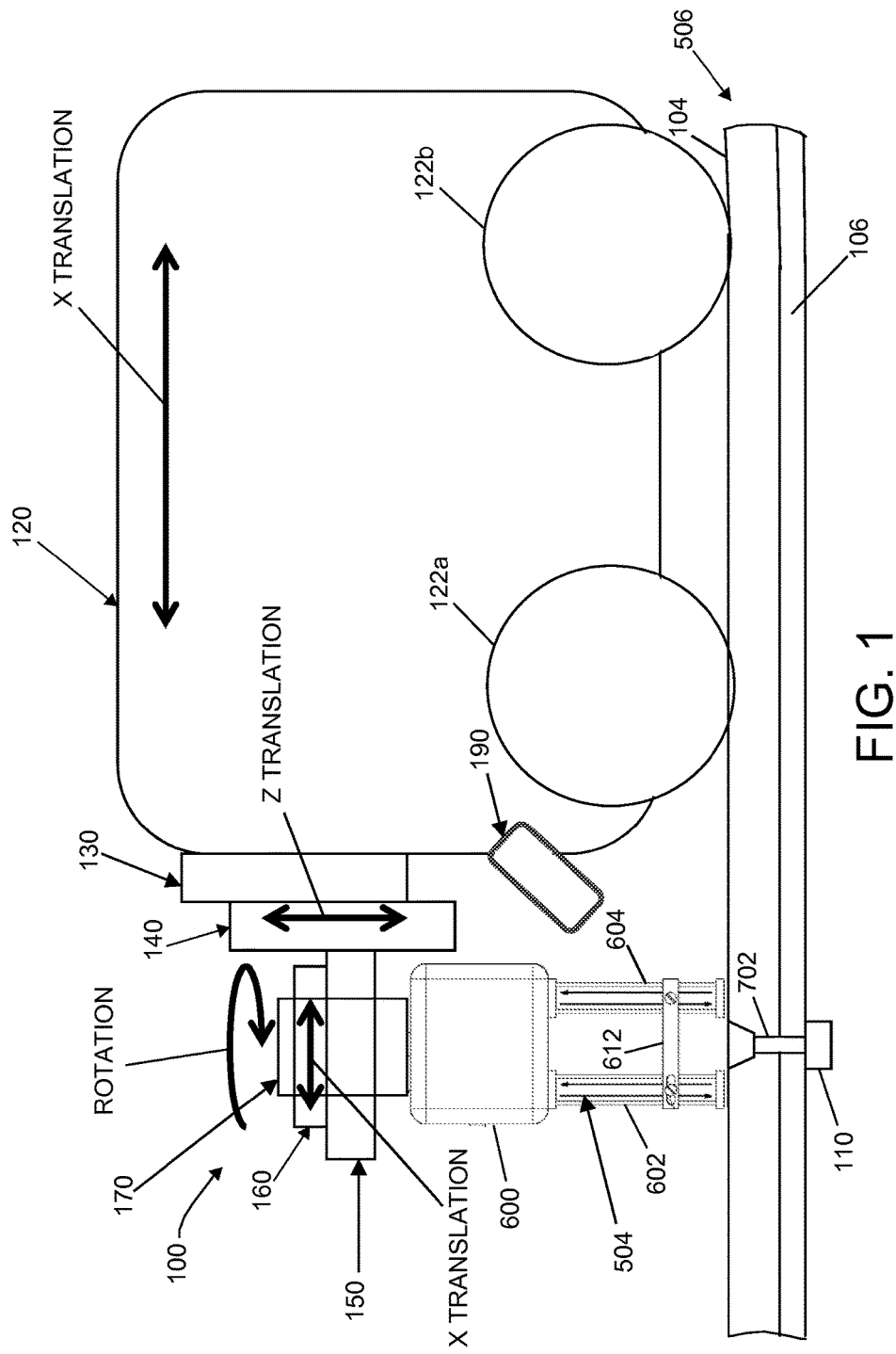

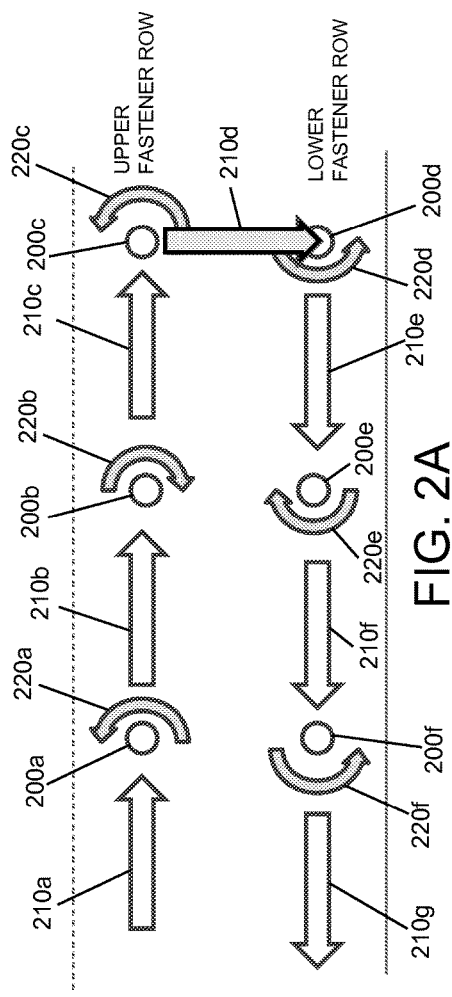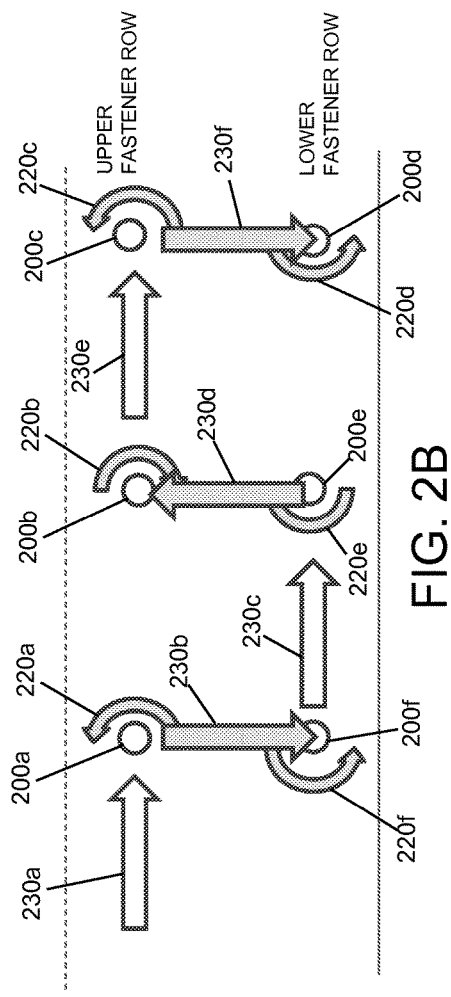

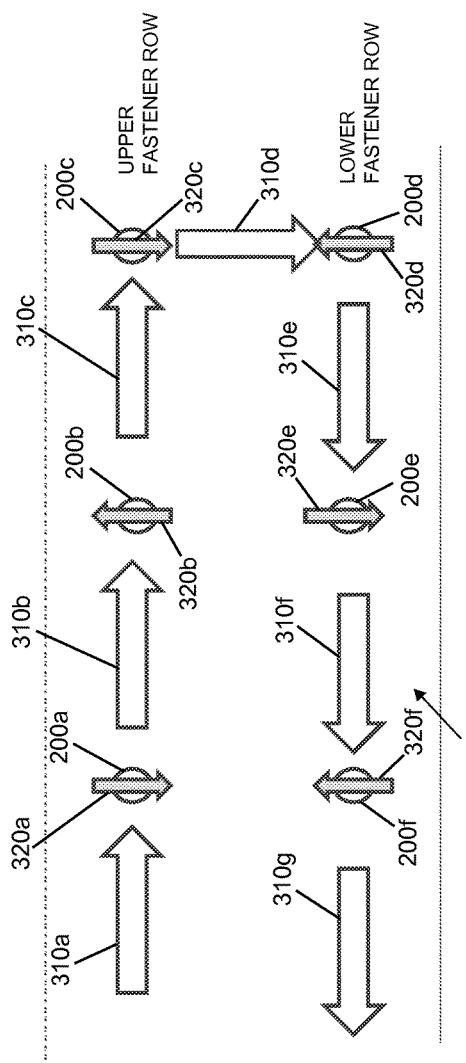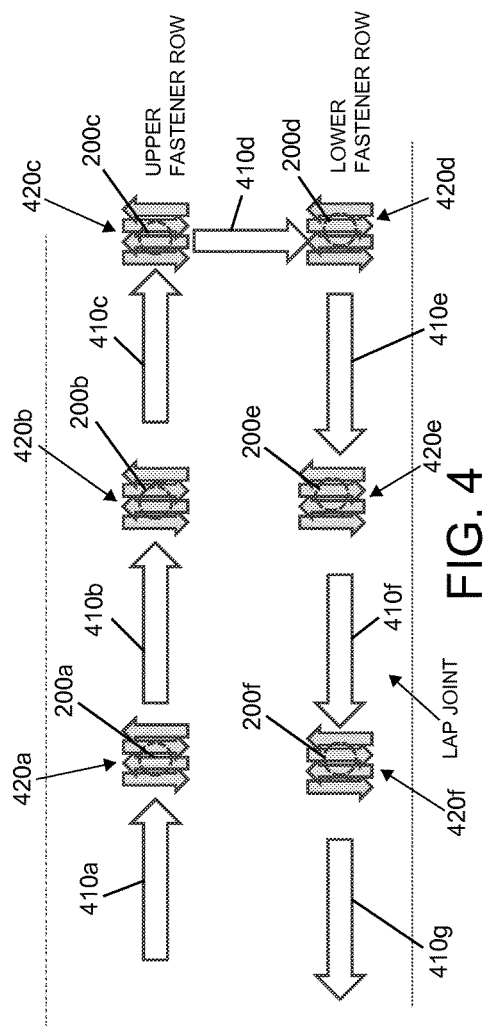

AUTOMATED DETECTION OF FATIGUE CRACKS AROUND FASTENERS USING MILLIMETER WAVEGUIDE PROBE

BACKGROUND

This disclosure generally relates to apparatus and methods for non-destructive inspection (NDI) of structural elements and, more particularly, relates to NDI techniques for detecting fatigue cracks around fasteners.

Non-destructive detection and evaluation of stress-induced fatigue cracks in metals may be practiced in many different environments, including surface transportation, aerospace transportation and power plants. For example, eddy current testing may be used to identify cracks that may not be visible. In some cases, paint may be removed to perform an inspection. Some paints or coatings have a conductive material that may make it more difficult to identify cracks when eddy current testing is used. Eddy current testing uses electromagnetic induction to identify cracks in conductive materials, such as metal skin panels. In particular, eddy current testing near features, such as fasteners, is affected by the electrical conductivity differences between the structure and the fastener. This difference may limit the sensitivity of this type of testing to detect inconsistencies. These types of inspections may require more time and expense than desired.

Another known technique for detecting cracks in metals uses a near-field millimeter wave (i.e., a wavelength range of 1-10 mm) waveguide probe. Millimeter wave signals do not penetrate through metals but are sensitive to the presence of metal surface discontinuities such as cracks. Advantageously, millimeter wave signals are able to propagate through dielectric materials, such as paint. Thus a waveguide probe can interrogate paint-covered metal surfaces. If a crack is present in the interrogated volume, the crack will produce a perturbation in the surface current density induced in the waveguide probe.

A known method of detecting cracks in metal around fasteners uses a hand-held waveguide probe. It would be desirable to provide an automated apparatus capable of performing millimeter wave crack detection, enabling crack detection that is faster, less labor intensive, more repeatable, and ergonomically safer than using a hand-held waveguide probe.

SUMMARY

The subject matter disclosed in detail below is directed to an automated high-speed method for inspecting metal around fasteners and a computer-controlled apparatus for performing that inspection method. In accordance with various embodiments, the apparatus comprises a multi-motion inspection head mounted on a scanning bridge, an end of a robotic arm, or a robotic crawler vehicle. The multi-motion inspection head comprises a millimeter waveguide probe and a motorized multi-stage probe placement head that is operable for displacing the waveguide probe along X, Y and Z axes to achieve multiple sequenced motions. The waveguide probe is attached to a mandrel that is rotatably coupled to an X-axis (or Y-axis) stage for rotation about the Z axis. Smart servo or stepper motors with feedback control are used to move the waveguide probe into place and then scan across or around a fastener head to inspect for cracks that may be under paint, extending outward from the fastener.

In accordance with one embodiment, the apparatus comprises various directional motorized stages that are sequenced and controlled for the specific motions needed to inspect fastener rows on aircraft fuselages. In alternative embodiments, the motorized stages can be sequenced and controlled for the specific motions needed to inspect fasteners on structures found in the nuclear power plant, oil drilling, shipbuilding and transportation industries.

In accordance with one inspection method, the scanning bridge, robotic arm, or crawler vehicle can be operated to move the waveguide probe to a location proximate to a first fastener or between first and second fasteners. While the scanning bridge, robotic arm, or crawler vehicle is inactive, the motorized multi-stage probe placement head can be operated to move the waveguide probe to a precise location overlying the first fastener, lower the waveguide probe to the inspection height, and then rotate or translate the waveguide probe during scanning of the area around the first fastener. After scanning of the first fastener has been completed, the motorized multi-stage probe placement head can be operated to move the waveguide probe to a precise location overlying the second fastener, where the foregoing process is repeated. After scanning of the second fastener has been completed, the scanning bridge, robotic arm, or crawler vehicle can be operated to move the waveguide probe to a location proximate to a third fastener or between third and fourth fasteners. Then the motorized multi-stage probe placement head can be operated to enable scanning of the areas around the third and fourth fasteners. All of the movements are controlled by a control computer.

In accordance with one embodiment, the control computer is programmed to perform fully automated inspection of fastener cracks on an aluminum skin of an aircraft fuselage, with the Z axis being parallel with the axis of the fastener. However, it should be appreciated that the automated apparatus and methods disclosed herein are suitable for inspection of metallic structures other than metallic aircraft fuselages.

One aspect of the subject matter disclosed in detail below is an apparatus for non-destructive inspection of metal around a fastener, comprising: a platform; a multi-stage probe placement head comprising a block assembly attached to the platform and first through third stages, the first stage being translatably coupled to the block assembly for translation along a first axis, the third stage being translatably coupled to the first stage for translation along a second axis orthogonal to the first axis, and the second stage being translatably coupled to the third stage for translation along a third axis orthogonal to the first and second axes; a mandrel rotatably coupled to the second stage of the multi-stage probe placement head for rotation about the first axis; and a waveguide probe attached to the mandrel. The platform may be a crawler vehicle, a scanning bridge or a robotic arm. The apparatus may further comprise a camera mounted to the platform, the camera being directed toward a volume of space under the multi-stage probe placement head. In the disclosed embodiments, the apparatus further comprises first through third motors mechanically coupled to the first through third stages respectively, and a fourth motor mechanically coupled to the mandrel, wherein the first stage will translate relative to the block assembly when the first motor is activated, the third stage will translate relative to the first stage when the third motor is activated, the second stage will translate relative to the third stage when the second motor is activated, and the mandrel will rotate relative to the second stage when the fourth motor is activated.

Another aspect of the subject matter disclosed herein is an apparatus for non-destructive inspection of metallic structure around a fastener, comprising: a platform; a multi-stage probe placement head comprising a block assembly attached to the platform, a first stage which is translatable relative to the block assembly along a first axis, and a second stage which is translatable relative to the block assembly along a second axis orthogonal to the first axis; a mandrel rotatably coupled to the second stage of the multi-stage probe placement head for rotation about the first axis; and a waveguide probe attached to the mandrel.

A further aspect of the disclosed subject matter is a method for non-destructive inspection of metal around a fastener, comprising: (a) moving a platform to a position whereat a waveguide probe movably coupled to the platform is in proximity to a fastener; (b) while the platform and waveguide probe are stationary, acquiring image data using a camera having a field of view that includes the fastener; (c) processing the image data to determine a location of the fastener in a frame of reference of the platform; (d) determining a difference between the current position and a start position of the waveguide probe in the frame of reference of the platform; (e) while the platform is stationary, moving the waveguide probe from the current position to the start position of the waveguide probe; and (f) while the platform is stationary, scanning at least a portion of an area around the fastener using the waveguide probe, scanning being started while the waveguide probe is in the start position.

In accordance with some embodiments of the method described in the preceding paragraph, a vertical axis midway between two apertures of the waveguide probe is approximately coaxial with a vertical axis through a center of the fastener when the waveguide probe is in the start position. In those embodiments, step (f) comprises rotating the waveguide probe.

In accordance with other embodiments, a vertical axis midway between two apertures of the waveguide probe is separated from a vertical axis through a center of the fastener when the waveguide probe is in the start position. In accordance with one embodiment, step (f) comprises translating the waveguide probe in a horizontal direction so that the vertical axis of the waveguide probe moves in a vertical plane which intersects the fastener. In accordance with another embodiment, step (f) comprises translating the waveguide probe horizontally so that the vertical axis of the waveguide probe follows a serpentine path in an area that includes the fastener.

Another aspect of the subject matter disclosed below is a method for non-destructive inspection of metal around a fastener, comprising: (a) moving a platform to a position whereat a waveguide probe movably coupled to the platform is in proximity to a fastener; (b) while the platform is stationary, moving the waveguide probe along a serpentine path that passes over the fastener; (c) while the waveguide probe is moving along the serpentine path, scanning an area around the fastener; (d) collecting wave signals from the waveguide probe; and (e) processing the collected wave signals to determine if those wave signals indicate the presence of a crack in the area around the fastener.

Yet another aspect of the subject matter disclosed in detail below is a system for non-destructive inspection of metal around a fastener, comprising: a platform comprising a plurality of movable parts and a first plurality of motors respectively mechanically coupled to the movable parts; a multi-stage probe placement head attached to the platform, the multi-stage probe placement head comprising an X-axis stage, a Y-axis stage and a Z-axis stage, the X-, Y- and Z-axis stages being respectively translatable in X, Y and Z directions; a second plurality of motors respectively mechanically coupled for driving translation of the X-, Y- and Z-axis stages; a waveguide probe rotatably coupled to the third stage of the multi-stage probe placement head, the waveguide probe being rotatable about the Z axis; a motor mechanically coupled for driving rotation of the waveguide probe about the Z axis; a camera mounted to the platform, the camera being directed toward a volume of space under the multi-stage probe placement head; and a computer system programmed to perform the following operations: processing imaging data acquired by the camera; controlling the motors; and controlling the waveguide probe to transmit wave signals. The platform may be a crawler vehicle, a scanning bridge or a robotic arm. The operation of processing imaging data acquired by the camera comprises recognizing imaging data representing an image of a fastener and then determining a position of the fastener in a frame of reference of the platform.

In accordance with some embodiments of the system described in the preceding paragraph, the operation of controlling the motors comprises activating and later de-activating at least one of the second plurality of motors to cause the waveguide probe to be moved to a start position at which a center axis of the waveguide probe intersects the fastener, and activating the motor mechanically coupled for driving rotation of the waveguide probe about the Z axis while the waveguide probe is in the start position, and wherein the operation of controlling the waveguide probe to transmit wave signals comprises activating the waveguide probe to transmit wave signals while the waveguide probe is rotating.

In accordance with other embodiments of the system, the operation of controlling the motors comprises activating and later de-activating at least one of the second plurality of motors to cause the waveguide probe to be moved to a first start position at which a central axis of the waveguide probe is not coaxial with a central axis of the fastener, and then activating and later de-activating the motor of the second plurality of motors which is mechanically coupled for driving translation of the Y-axis stage to cause the waveguide probe to translate in a first Y direction from the first start position to a first stop position, and the operation of controlling the waveguide probe to transmit wave signals comprises activating the waveguide probe to transmit wave signals while the waveguide probe is moving from the first start position to the first stop position.

In a variation of the embodiments described in the preceding paragraph, the operation of controlling the motors further comprises activating and later de-activating the motor of the second plurality of motors which is mechanically coupled for driving translation of the X-axis stage to cause the waveguide probe to translate in an X direction from the first stop position to a second start position, and thereafter activating and later de-activating the motor of the second plurality of motors which is mechanically coupled for driving translation of the Y-axis stage to cause the waveguide probe to translate in a second Y direction opposite to the first Y direction from the second start position to a second stop position, and the operation of controlling the waveguide probe to transmit wave signals further comprises activating the waveguide probe to transmit wave signals while the waveguide probe is moving from the second start position to the second stop position.

Other aspects of apparatus and methods for automated millimeter wave crack detection are disclosed below.

BRIEF DESCRIPTION OF THE DRAWINGS

FIG. 1 is a diagram representing a side view of a crawler vehicle carrying a waveguide probe for detecting cracks around fasteners in accordance with one embodiment.

FIG. 2A is a diagram showing two rows of fasteners and arrows indicating waveguide probe movements in accordance with one possible implementation. These waveguide probe movements can be used when the crack direction is not generally known.

FIG. 2B is a diagram showing two rows of fasteners and arrows indicating waveguide probe movements in accordance with another possible implementation. These waveguide probe movements can be used when the crack direction is not generally known.

FIG. 3 is a diagram showing two rows of fasteners and arrows indicating waveguide probe movements in accordance with a third possible implementation. These waveguide probe movements can be used when the crack direction is along the fuselage of an aircraft.

FIG. 4 is a diagram showing two rows of fasteners and arrows indicating waveguide probe movements in accordance with a fourth possible implementation. These waveguide probe movements, which include raster-type scanning, can be used when the crack direction is along the fuselage of an aircraft.

Reference will hereinafter be made to the drawings in which similar elements in different drawings bear the same reference numerals.

DETAILED DESCRIPTION

Figure 5:
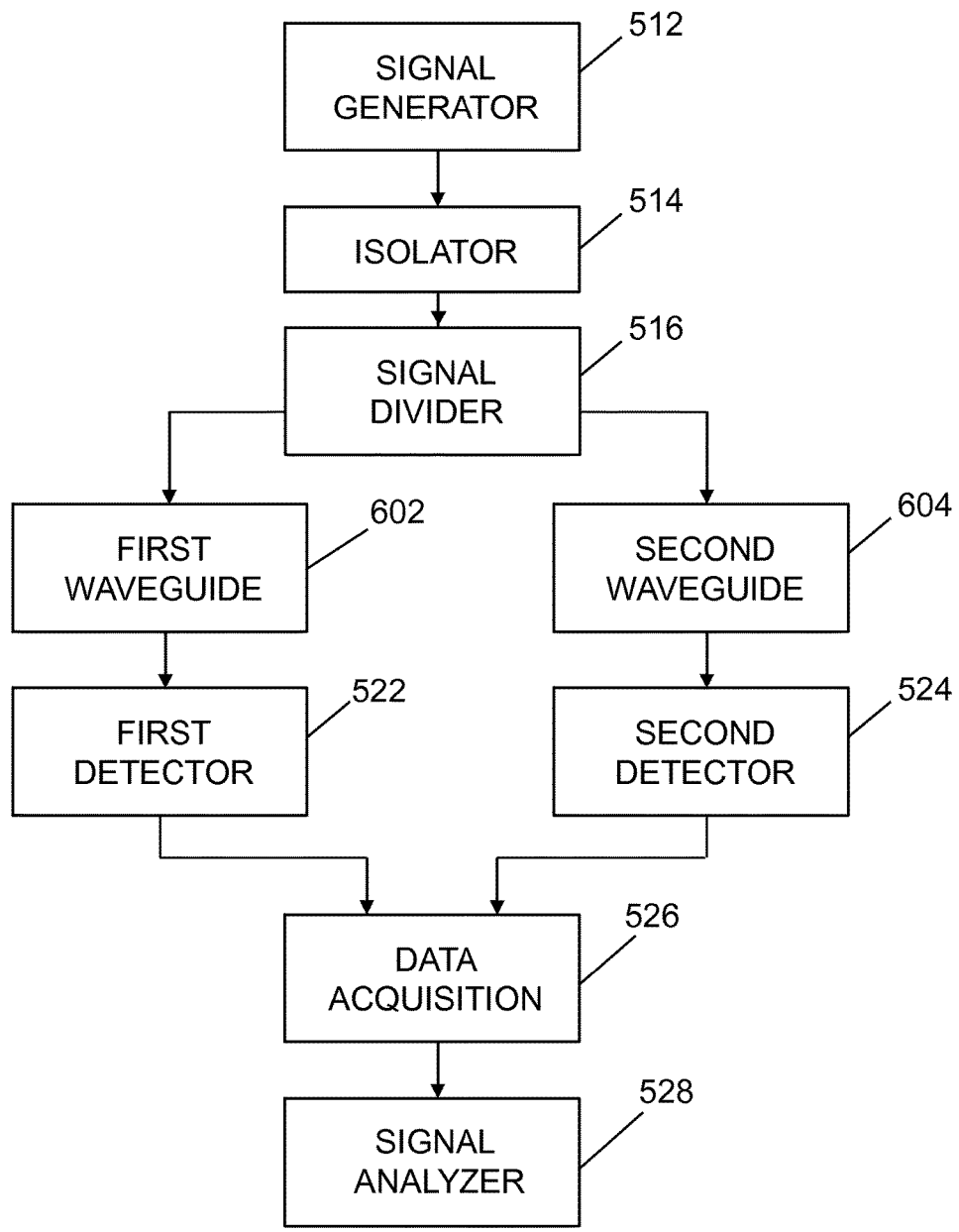
FIG. 5 is a block diagram identifying components of a millimeter wave crack detection system.

Various embodiments and implementations will be described with reference to millimeter wave detection of cracks around fasteners in metal aircraft fuselages. However, it should be appreciated that the apparatus and methods disclosed in detail below can also be used to detect other types of incongruities around fasteners. It should be further appreciated that the apparatus and methods disclosed in detail below can also be used to detect incongruities (such as cracks) in other types of metal structures, such as components of nuclear power plants, ships, trains, oil drilling probe placement heads, and so forth.

FIG. 1 is a diagram representing a side view of a crawler vehicle 120 having a multi-stage probe placement head 100 mounted on its forward end in accordance with one embodiment. The multi-stage probe placement head 100 supports a waveguide probe 504, which can be used to detect cracks in metal structure around a fastener. In the example depicted in FIG. 1, the object being inspected is a fuselage skin 506 comprises overlapping metallic layers 104 and 106 which are fastened together by a multiplicity of fasteners. The fasteners are typically arranged in rows. Only one fastener 702 is shown in FIG. 1. The fastener 702 is secured in aligned holes in layers 104, 106 by means of a collar. The waveguide probe 504 is shown in a position suitable for inspecting the area around the fastener 702, i.e., a center axis of the waveguide probe 504 is coaxial with a center axis of the fastener 702. During an inspection procedure, the waveguide probe 504 transmits millimeter wave signals which interrogate the metal surrounding the fastener 702. Since millimeter wave signals penetrate through dielectric materials, such as paint, paint-covered metal surfaces can be inspected. The waveguide probe does not need to be in contact with the surface being inspected.

The crawler vehicle 120 may take the form of a remotely operated vacuum-enabled robot capable of moving along a surface which is non-horizontal using suction devices (e.g., fans driven by motors mounted on a frame of the crawler vehicle 120). In the embodiment depicted in FIG. 1, only two wheels 122a and 122b of a set of four wheels are visible. Rotation of Mecanum type wheels driven by their respective motors (not shown) mounted on the frame of the crawler vehicle 120 enable holonomic motion. Holonomic motion, where turning and translating are decoupled, enables scanning in any direction within the X-Y plane. The crawler vehicle 120 may be steered for movement in an X-Y plane, with the X axis being parallel to a row of fasteners being inspected. Movement of the crawler vehicle 120 along a row of fasteners is indicated by the long double-headed arrows labeled "X TRANSLATION" in FIG. 1.

A video camera 190 is mounted on the crawler vehicle 120. The camera can be oriented so that its field of view will include a volume of space under the multi-stage probe placement head 100. The video camera 190 captures imaging data and sends that imaging data to a computer (not shown in FIG. 1). the communication channel between the video camera 190 and the computer can be via an electrical cable or wireless. The computer will use the imaging feedback provided by the video camera 190 to control precision alignment of the waveguide probe 504 with the fastener 702 to be inspected.

Still referring to FIG. 1, the multi-stage probe placement head 100 comprises a block assembly 130 attached to the crawler vehicle 120, a Z-axis stage 140 translatably coupled to the block assembly 130, a X-axis stage 150 translatably coupled to the Z-axis stage 140, and a Y-axis stage 160 translatably coupled to the X-axis stage 150. A mandrel 170 is rotatably coupled to the Y-axis stage 160. The waveguide probe 504 is attached to the mandrel 170, i.e., the mandrel 170 and waveguide probe 504 rotate in unison. The three stages of the probe placement head 100 can be driven by motors for causing the waveguide probe 504 to move in the X, Y or Z directions respectively. The Z-axis stage 140 is used to raise or lower the waveguide probe 504. The X-axis stage 150 and Y-axis stage 160 provide precision motion for centering the waveguide probe 504 on the fastener 702. The X, Y and Z axes are mutually orthogonal axes in the coordinate frame of reference of the crawler vehicle 120. In an ideal inspection scenario, the Z axis of the crawler vehicle 120 will be parallel to the center line of the fastener being inspected. Multiple motions using smart servo or stepper motors (not shown in FIG. 1) with feedback control (based on imaging data acquired by video camera 190) are used to precisely position the waveguide probe 504 relative to the fastener 702. When proper placement has been realized, the waveguide probe 504 can then be translated or rotated to scan across or around the head of the fastener 702 to inspect for cracks in the fuselage skin 506. To enable rotation of the waveguide probe 504, the mandrel 170 can be driven to rotate by a stepper motor (not shown in FIG. 1).

As will be explained in more detail below with reference to FIG. 6, the waveguide probe 504 comprises a housing 600 which is attached to the mandrel 170. A pair of waveguides 602 and 604 have respective proximal ends coupled to the housing 600. The waveguides 602, 604 extend in parallel from the housing 600 to the surface of the metal structure to be inspected. The waveguides 602 and 604 are connected by a bar 612. The distal ends of the waveguides 602, 604 have waveguide apertures which emit millimeter wave signals during rotation or translation of the waveguide probe 504.

In the scenario depicted in FIG. 1, the millimeter wave signals will penetrate any dielectric coating on the top surface of the fuselage skin 506 and then interrogate the metal around the fastener 702. Crack detection is based on the perturbation that a crack will produce in the surface current density induced on the metal skin by the millimeter wave signals emitted by the waveguide probe 504. The induced surface current on the metal surface creates a reflected wave and subsequently a standing wave inside the waveguide probe. As will be explained in more detail below, the presence of a crack inside the waveguide aperture perturbs the surface current density and changes the properties of the reflected and standing waves. Changes in the properties of the standing wave pattern inside the waveguide can indicate the presence of a crack.

The system depicted in FIG. 1 is capable of inspecting the metal around fasteners arranged in rows, for example, on an aircraft fuselage, using a waveguide probe 504 that is moved from fastener to fastener. While FIG. 1 shows the waveguide probe 504 aligned with the fastener 702, in general the crawler vehicle 120 will move from one fastener to the next after each scan has been completed. When the waveguide probe 504 is in proximity to the next fastener 702, then the video camera 190 captures imaging data that is used to determine the position of the waveguide probe 504 relative to the fastener 702. Then X- and Y-stage motors (not shown) on the multi-stage probe placement head 100 can be operated to translate the waveguide probe 504 in the X and/or Y directions until the waveguide probe 504 and fastener 702 are aligned. Then the waveguide probe can be lowered into the start position and the metal around the fastener 702 can be scanned. The sequence of motions may be varied in accordance with specific implementations to be described in detail below with reference to FIGS. 2A, 2B, 3 and 4.

In the scenario depicted in FIG. 1, the waveguide probe 504 is shown in a starting position in which a center line of the waveguide probe 504 is approximately coaxial with the center line of the fastener 702. The double-headed arrows in FIG. 1 indicate various movements which resulted in the scenario depicted in FIG. 1. First, the crawler vehicle was moved from a position where the waveguide probe 504 was not in proximity to the fastener 702 to a position where the waveguide probe 504 was in proximity to but not yet aligned with the fastener 702 (this position is not shown in FIG. 1). In the example depicted, the crawler vehicle 120 was translated along the X axis, which is parallel to the row of fasteners to which fastener 702 belongs. When the fastener 702 was within the field of view of the video camera 190, the crawler vehicle 120 was commanded to stop. While the crawler vehicle 120 and the waveguide probe 504 were stationary, the video camera 190 was activated to acquire image data representing the field of view, which included the head of the fastener 702. That image data was then processed by a computer (not shown in FIG. 1) using pattern recognition software to determine a location of a center line of the fastener 702 in a frame of reference of the crawler vehicle 120. The computer then used the location of the fastener center line to determine a difference between the current position and the start position of the waveguide probe 504 in the frame of reference of the crawler vehicle 120. Thereafter, while the crawler vehicle 120 was stationary, the waveguide probe 504 was moved in the X and/or Y directions from its current position to a position directly above the start position (movement in the X direction is indicated by the short double-headed arrow labeled "X TRANSLATION" in FIG. 1). Then the waveguide probe 504 was lowered to the start position by activating the motor (not shown) mechanically coupled to the Z-axis stage 140 (movement in the Z direction is indicated by the short double-headed arrow labeled "Z TRANSLATION").

In the start position depicted in FIG. 1, the center line of the waveguide probe 504 is coaxial with the fastener center line. (In alternative implementations, the start position is selected such that the center line of the waveguide probe 504 is spaced apart from the fastener by a short distance.) Then, while the crawler vehicle 120 is stationary, the waveguide probe 504 is activated to scan at least a portion of the area around the fastener 702. Starting at the start position, the waveguide probe 504 is either rotated (as indicated by the curved double-headed arrow label "ROTATION") through a predetermined angle or translated in the X direction (not indicated in FIG. 1) a predetermined distance. Both waveguides 602 and 604 of the waveguide probe 504 emit millimeter wave signals toward respective areas near the fastener 702 during the scanning movement. The resulting standing waves inside the waveguides 602, 604 are detected and then analyzed to determine whether cracks are present in the metal around the fastener 702.

Scanning a row of fasteners by rotating the waveguide probe 504 when it is aligned with and overlying each fastener is especially useful in cases where the direction of surface-breaking cracks emanating from the fastener is not generally known. The crawler vehicle (or other platform, such as a scanning bridge or a robotic arm) can be set at the first fastener in the row, and oriented so it can move along the fastener row. The camera mounted on the platform is used to capture an image of the fastener head. Pattern recognition software can be used to identify the circular shape of the fastener head and finds its center (i.e., the center line of the fastener). The X- and/or Y-axis stages can be driven to adjust the fine position of the waveguide probe so that its center line is approximately coaxial with the center line of the fastener. If needed, the Z-axis stage is adjusted so that the apertures of the waveguides are just above the surface of the area around the fastener head. Then the waveguide probe can be rotated at least 180 degrees around the fastener, while the system takes a measurement. All signals are collected around the fastener. If the area around the fastener produces signals above a predetermined threshold, that fastener is tagged in the data set for repair and optionally marked with a pen or paint marker dropped adjacent to the fastener (the threshold is determined using a reference standard with a range of cracks). Data (e.g., signal, fastener location number, and data tag indicating fasteners with crack indications) is collected and stored for retrieval, analysis, or data manipulation, such as gating for maximum signal in order to size cracks. Then the crawler vehicle (or other platform) moves along the fastener row to the next fastener. The inspection can be done one row at a time, covering both rows in two passes. Alternatively, Y-axis movement of the crawler vehicle (or other platform) can enable one pass while scanning both rows on a single lap joint.

FIG. 2A is a diagram showing two rows of fasteners 200a-200f. For ease of discussion, it will be assumed that the rows of fasteners are mutually parallel. The straight arrows 210a-210g indicate respective movements of the waveguide probe (along the X axis) during coarse positioning (due to movement of the supporting platform; the waveguide probe is not moving relative to the platform) in accordance with one possible implementation. The curved arrows 220a-220f indicate successive rotations of the waveguide probe at successive positions overlying and aligned with the fasteners 200a-200f. The fine positioning movements of the waveguide probe, attributable to movements by one or more stages of the multi-stage probe placement head, are not indicated by arrows in FIG. 2A. These waveguide probe movements can be used when the crack direction is not generally known.

More specifically, steps of a method for scanning two rows of fasteners using a millimeter waveguide probe, as partially depicted in FIG. 2A, may comprise the following steps.

(1) The platform is translated in a first direction along an X axis parallel to the upper row of fasteners, as indicated by arrow 210a, until the waveguide probe is positioned in proximity to fastener 200a.

(2) The position of the waveguide probe relative to the platform is adjusted to place the waveguide probe in a start scan position (i.e., aligned with and directly above the fastener 200a), which adjustments may comprise translation along one or more of the X, Y and Z axes (not indicated by arrows in FIG. 2A).

(3) The waveguide probe is rotated to effect scanning of the area surrounding fastener 200a. This rotation is indicated by arrow 220a in FIG. 2A.

(4) The platform is translated in the first direction, as indicated by arrow 210b, until the waveguide probe is positioned in proximity to fastener 200b in the upper row.

(5) The position of the waveguide probe relative to the platform is adjusted to place the waveguide probe in a start scan position (i.e., aligned with and directly above the fastener 200b), which adjustments may comprise translation along one or more of the X, Y and Z axes (not indicated by arrows in FIG. 2A).

(6) The waveguide probe is rotated to effect scanning of the area surrounding fastener 200b. This rotation is indicated by arrow 220b in FIG. 2A.

(7) The platform is translated in the first direction, as indicated by arrow 210c, until the waveguide probe is positioned in proximity to fastener 200c in the upper row.

(8) The position of the waveguide probe relative to the platform is adjusted to place the waveguide probe in a start scan position (i.e., aligned with and directly above the fastener 200c), which adjustments may comprise translation along one or more of the X, Y and Z axes (not indicated by arrows in FIG. 2A).

(9) The waveguide probe is rotated to effect scanning of the area surrounding fastener 200c. This rotation is indicated by arrow 220c in FIG. 2A.

(10) The platform is translated in a second direction along the Y axis and perpendicular to the first direction, as indicated by arrow 210d, until the waveguide probe is positioned in proximity to fastener 200d in the lower row.

(11) The position of the waveguide probe relative to the platform is adjusted to place the waveguide probe in a start scan position (i.e., aligned with and directly above the fastener 200d), which adjustments may comprise translation along one or more of the X, Y and Z axes (not indicated by arrows in FIG. 2A).

(12) The waveguide probe is rotated to effect scanning of the area surrounding fastener 200d. This rotation is indicated by arrow 220d in FIG. 2A.

(13) The platform is translated in a third direction opposite to the first direction, as indicated by arrow 210e, until the waveguide probe is positioned in proximity to fastener 200e in the lower row.

(14) The position of the waveguide probe relative to the platform is adjusted to place the waveguide probe in a start scan position (i.e., aligned with and directly above the fastener 200e), which adjustments may comprise translation along one or more of the X, Y and Z axes (not indicated by arrows in FIG. 2A).

(15) The waveguide probe is rotated to effect scanning of the area surrounding fastener 200e. This rotation is indicated by arrow 220e in FIG. 2A.

(16) The platform is translated in the third direction, as indicated by arrow 210f, until the waveguide probe is positioned in proximity to fastener 200f in the lower row.

(17) The position of the waveguide probe relative to the platform is adjusted to place the waveguide probe in a start scan position (i.e., aligned with and directly above the fastener 200f), which adjustments may comprise translation along one or more of the X, Y and Z axes (not indicated by arrows in FIG. 2A).

(18) The waveguide probe is rotated to effect scanning of the area surrounding fastener 200f. This rotation is indicated by arrow 220f in FIG. 2A.

(19) The platform is translated in the third direction, as indicated by arrow 210g, until the waveguide probe is positioned in proximity to the next fastener (not shown in FIG. 2A) in the lower row.

FIG. 2B is a diagram showing two rows of fasteners 200a-200f. The straight arrows 230a-230g indicate respective movements of the waveguide probe (in the X axis) during coarse positioning (due to movement of the supporting platform; the waveguide probe is not moving relative to the platform) in accordance with another possible implementation. The curved arrows 220a-220f again indicate successive rotations of the waveguide probe at successive positions overlying and aligned with the fasteners 200a-200f. The fine positioning movements of the waveguide probe, attributable to movements by one or more stages of the multi-stage probe placement head, are not indicated by arrows in FIG. 2B. The method depicted in FIG. 2B differs from the method depicted in FIG. 2A in the order in which the two rows of fasteners are inspected. These waveguide probe movements can be used when the crack direction is not generally known.

More specifically, steps of a method for scanning two rows of fasteners using a millimeter waveguide probe, as partially depicted in FIG. 2B, may comprise the following steps.

(1) The platform is translated in a first direction along an X axis parallel to the upper row of fasteners, as indicated by arrow 230a, until the waveguide probe is positioned in proximity to fastener 200a.

(2) The position of the waveguide probe relative to the platform is adjusted to place the waveguide probe in a start scan position (i.e., aligned with and directly above the fastener 200a), which adjustments may comprise translation along one or more of the X, Y and Z axes (not indicated by arrows in FIG. 2B).

(3) The waveguide probe is rotated to effect scanning of the area surrounding fastener 200a. This rotation is indicated by arrow 220a in FIG. 2B.

(4) The platform is translated in a second direction along the Y axis and perpendicular to the first direction, as indicated by arrow 230b, until the waveguide probe is positioned in proximity to fastener 200f in the lower row.

(5) The position of the waveguide probe relative to the platform is adjusted to place the waveguide probe in a start scan position (i.e., aligned with and directly above the fastener 200f), which adjustments may comprise translation along one or more of the X, Y and Z axes (not indicated by arrows in FIG. 2B).

(6) The waveguide probe is rotated to effect scanning of the area surrounding fastener 200f. This rotation is indicated by arrow 220f in FIG. 2B.

(7) The platform is translated in the first direction, as indicated by arrow 230c, until the waveguide probe is positioned in proximity to fastener 200e.

(8) The position of the waveguide probe relative to the platform is adjusted to place the waveguide probe in a start scan position (i.e., aligned with and directly above the fastener 200e), which adjustments may comprise translation along one or more of the X, Y and Z axes (not indicated by arrows in FIG. 2B).

(9) The waveguide probe is rotated to effect scanning of the area surrounding fastener 200e. This rotation is indicated by arrow 220e in FIG. 2B.

(10) The platform is translated in a third direction opposite to the second direction, as indicated by arrow 230d, until the waveguide probe is positioned in proximity to fastener 200b.

(11) The position of the waveguide probe relative to the platform is adjusted to place the waveguide probe in a start scan position (i.e., aligned with and directly above the fastener 200b), which adjustments may comprise translation along one or more of the X, Y and Z axes (not indicated by arrows in FIG. 2B).

(12) The waveguide probe is rotated to effect scanning of the area surrounding fastener 200b. This rotation is indicated by arrow 220b in FIG. 2B.

(13) The platform is translated in the first direction, as indicated by arrow 230e, until the waveguide probe is positioned in proximity to fastener 200c.

(14) The position of the waveguide probe relative to the platform is adjusted to place the waveguide probe in a start scan position (i.e., aligned with and directly above the fastener 200c), which adjustments may comprise translation along one or more of the X, Y and Z axes (not indicated by arrows in FIG. 2B).

(15) The waveguide probe is rotated to effect scanning of the area surrounding fastener 200c. This rotation is indicated by arrow 220c in FIG. 2B.

(16) The platform is translated in the second direction, as indicated by arrow 230f, until the waveguide probe is positioned in proximity to fastener 200d.

(17) The position of the waveguide probe relative to the platform is adjusted to place the waveguide probe in a start scan position (i.e., aligned with and directly above the fastener 200d), which adjustments may comprise translation along one or more of the X, Y and Z axes (not indicated by arrows in FIG. 2B).

(18) The waveguide probe is rotated to effect scanning of the area surrounding fastener 200d. This rotation is indicated by arrow 220d in FIG. 2B.

Scanning a row of fasteners by translating the waveguide probe 504 when it is in proximity to each fastener is especially useful in cases where the direction of surface-breaking cracks emanating from the fastener is parallel to a horizontal row of fasteners on a fuselage of an aircraft. The crawler vehicle (or other platform, such as a scanning bridge or a robotic arm) can be set at the first fastener in the row, and oriented so it can move along the fastener row. The camera mounted on the platform is used to capture an image of the fastener head. Pattern recognition software can be used to identify the circular shape of the fastener head and finds its center (i.e., the center line of the fastener). The X- and/or Y-axis stages can be driven to adjust the fine position of the waveguide probe so that its center line is approximately coaxial with the center line of the fastener. If needed, the Z-axis stage is adjusted so that the apertures of the waveguides are just above the surface of the area around the fastener head. Then the waveguide probe can be translated across the fastener, from one side to the other, with feet passing adjacent to the fastener, while the system takes a measurement. All signals are collected on both sides of the fastener. If the area around the fastener produces signals above a predetermined threshold, that fastener is tagged in the data set for repair and optionally marked with a pen or paint marker dropped adjacent to the fastener (the threshold is determined using a reference standard with a range of cracks). Data (e.g., signal, fastener location number, and data tag indicating fasteners with crack indications) is collected and stored for retrieval, analysis, or data manipulation, such as gating for maximum signal in order to size cracks. Then the crawler vehicle (or other platform) moves along the fastener row to the next fastener. The inspection can be done one row at a time, covering both rows in two passes. Alternatively, Y-axis movement of the crawler vehicle (or other platform) can enable one pass while scanning both rows on a single lap joint.

FIG. 3 is a diagram showing two rows of fasteners 200a-200f. The straight arrows 310a-310g indicate respective movements of the waveguide probe during coarse positioning (due to movement of the supporting platform; the waveguide probe is not moving relative to the platform) in accordance with another possible implementation. The short arrows 320a-320f indicate successive vertical translations of the waveguide probe at successive positions overlying and aligned with the fasteners 200a-200f. The fine positioning movements of the waveguide probe, attributable to movements by one or more stages of the multi-stage probe placement head, are not indicated by arrows in FIG. 3. These waveguide probe movements can be used when the crack direction is parallel to a horizontal line of the fuselage of an aircraft.

More specifically, steps of a method for scanning two rows of fasteners using a millimeter waveguide probe, as partially depicted in FIG. 3, may comprise the steps listed below. For purposes of this example only, the term "start scan position" means that the probe center line intersects or nearly intersects a diametral line which extends across the head of the fastener and is perpendicular to the horizontal line of the fuselage.

(1) The platform is translated in a first direction along the X axis parallel to the upper row of fasteners, as indicated by arrow 310a, until the waveguide probe is positioned in proximity to fastener 200a in the upper row.

(2) The position of the waveguide probe relative to the platform is adjusted to place the waveguide probe in a start scan position relative to fastener 200a, which adjustments may comprise translation along one or more of the X, Y and Z axes (not indicated by arrows in FIG. 3).

(3) The waveguide probe is translated in a second direction along the Y axis and perpendicular to the first direction to effect scanning of at least a portion of the area surrounding fastener 200a. This translation is indicated by arrow 320a in FIG. 3.

(4) The platform is translated in the first direction, as indicated by arrow 310b, until the waveguide probe is positioned in proximity to fastener 200b in the upper row.

(5) The position of the waveguide probe relative to the platform is adjusted to place the waveguide probe in a start scan position relative to fastener 200b, which adjustments may comprise translation along one or more of the X, Y and Z axes (not indicated by arrows in FIG. 3).

(6) The waveguide probe is translated in a third direction opposite to the second direction to effect scanning of at least a portion of the area surrounding fastener 200b. This translation is indicated by arrow 320b in FIG. 3.

(7) The platform is translated in the first direction, as indicated by arrow 310c, until the waveguide probe is positioned in proximity to fastener 200c in the upper row.

(8) The position of the waveguide probe relative to the platform is adjusted to place the waveguide probe in a start scan position relative to fastener 200c, which adjustments may comprise translation along one or more of the X, Y and Z axes (not indicated by arrows in FIG. 3).

(9) The waveguide probe is translated in the second direction to effect scanning of at least a portion of the area surrounding fastener 200c. This translation is indicated by arrow 320c in FIG. 3.

(10) The platform is translated in the second direction, as indicated by arrow 310d, until the waveguide probe is positioned in proximity to fastener 200d in the lower row.

(11) The position of the waveguide probe relative to the platform is adjusted to place the waveguide probe in a start scan position relative to fastener 200d, which adjustments may comprise translation along one or more of the X, Y and Z axes (not indicated by arrows in FIG. 3).

(12) The waveguide probe is translated in the third direction to effect scanning of at least a portion of the area surrounding fastener 200d. This translation is indicated by arrow 320d in FIG. 3.

(13) The platform is translated in a fourth direction opposite to the first direction, as indicated by arrow 310e, until the waveguide probe is positioned in proximity to fastener 200e in the lower row.

(14) The position of the waveguide probe relative to the platform is adjusted to place the waveguide probe in a start scan position relative to fastener 200e, which adjustments may comprise translation along one or more of the X, Y and Z axes (not indicated by arrows in FIG. 3).

(15) The waveguide probe is translated in the second direction to effect scanning of at least a portion of the area surrounding fastener 200e. This translation is indicated by arrow 320e in FIG. 3.

(16) The platform is translated in the fourth direction, as indicated by arrow 310f, until the waveguide probe is positioned in proximity to fastener 200f in the lower row.

(17) The position of the waveguide probe relative to the platform is adjusted to place the waveguide probe in a start scan position relative to fastener 200f, which adjustments may comprise translation along one or more of the X, Y and Z axes (not indicated by arrows in FIG. 3).

(18) The waveguide probe is translated in the third second direction to effect scanning of at least a portion of the area surrounding fastener 200f. This translation is indicated by arrow 320f in FIG. 3.

(19) The platform is translated in the fourth direction, as indicated by arrow 310g, until the waveguide probe is positioned in proximity to the next fastener (not shown in FIG. 3) in the lower row.

Raster scanning the area around each fastener in a horizontal row is especially useful in cases where the direction of surface-breaking cracks emanating from the fastener is parallel to the fastener row. The crawler vehicle (or other platform, such as a scanning bridge or a robotic arm) can be set at the first fastener in the row, and oriented so it can move along the fastener row. If needed, the Z-axis stage is adjusted so that the apertures of the waveguides are just above the surface of the area to be inspected. The X- and Y-axis stages of the multi-stage probe placement head are then sequentially activated to move the waveguide probe along a serpentine path to effect raster scanning of the area around the fastener. All signals are collected in a grid at X and Y positions at a pre-selected spacing. Fasteners surrounded by an area which produced wave signals above a predetermined threshold are tagged in the data set for repair and optionally marked with a pen or paint marker dropped adjacent to the fastener (the threshold is determined using a reference standard with a range of cracks). Data (full wave form, maximum difference signal, fastener location number, and data tag indicating fasteners with crack indications) is collected and stored for retrieval, analysis, or data manipulation, such as gating for maximum signal in order to size cracks. An image of the maximum difference wave signal is created, displayed on a computer monitor, and stored for later retrieval. Then the platform is moved along the fastener row to the next fastener in the row. This process can be repeated until all fasteners in the row have been inspected and imaged.

FIG. 4 is a diagram showing two rows of fasteners 200a-200f. The straight arrows 410a-410g again indicate respective movements of the waveguide probe during movement of the platform on which the waveguide probe is mounted. The sets of oppositely directed short arrows 420a-420f indicate successive rastered scans executed by the waveguide probe at successive starting positions in proximity to the fasteners 200a-200f. These waveguide probe movements can be used when the crack direction is parallel to a horizontal line of the fuselage of an aircraft and when complete C-scan type images of the fastener heads are desired.

More specifically, steps of a method for scanning two rows of fasteners using a millimeter waveguide probe, as partially depicted in FIG. 4, may comprise the steps listed below. For purposes of this example only, the term "start scan position" means that the probe center line is spaced apart from the diametral line which extends across the head of the fastener and is perpendicular to the horizontal line of the fuselage.

(1) The platform is translated in a first direction along the X axis parallel to the upper row of fasteners, as indicated by arrow 410a, until the waveguide probe is positioned in proximity to fastener 200a in the upper row.

(2) The position of the waveguide probe relative to the platform is adjusted to place the waveguide probe in a start scan position relative to fastener 200a, which adjustments may comprise translation along the Z axis (not indicated by an arrow in FIG. 4).

(3) The waveguide probe is alternatingly translated along the X and Y axes so that it follows a serpentine path to effect a raster scan of the area surrounding fastener 200a. Only the back and forth translations along the Y axis are indicated by arrows 420a in FIG. 4 (the connecting short translations along the X axis are not shown).

(4) The platform is translated in the first direction, as indicated by arrow 410b, until the waveguide probe is positioned in proximity to fastener 200b in the upper row.

(5) The position of the waveguide probe relative to the platform is adjusted to place the waveguide probe in a start scan position relative to fastener 200b, which adjustments may comprise translation along the Z axis (not indicated by an arrow in FIG. 4).

(6) The waveguide probe is alternatingly translated along the X and Y axes so that it follows a serpentine path to effect a raster scan of the area surrounding fastener 200b. Only the back and forth translations along the Y axis are indicated by arrows 420b in FIG. 4.

(7) The platform is translated in the first direction, as indicated by arrow 410c, until the waveguide probe is positioned in proximity to fastener 200c in the upper row.

(8) The position of the waveguide probe relative to the platform is adjusted to place the waveguide probe in a start scan position relative to fastener 200c, which adjustments may comprise translation along the Z axis (not indicated by an arrow in FIG. 4).

(9) The waveguide probe is alternatingly translated along the X and Y axes so that it follows a serpentine path to effect a raster scan of the area surrounding fastener 200c. Only the back and forth translations along the Y axis are indicated by arrows 420c in FIG. 4.

(10) The platform is translated along the Y axis, as indicated by arrow 410d, until the waveguide probe is positioned in proximity to fastener 200d in the lower row.

(11) The position of the waveguide probe relative to the platform is adjusted to place the waveguide probe in a start scan position relative to fastener 200d, which adjustments may comprise translation along the Z axis (not indicated by an arrow in FIG. 4).

(12) The waveguide probe is alternatingly translated along the X and Y axes so that it follows a serpentine path to effect a raster scan of the area surrounding fastener 200d. Only the back and forth translations along the Y axis are indicated by arrows 420d in FIG. 4.

(13) The platform is translated along the X axis in a direction opposite to the first direction, as indicated by arrow 410e, until the waveguide probe is positioned in proximity to fastener 200e in the lower MM.

(14) The position of the waveguide probe relative to the platform is adjusted to place the waveguide probe in a start scan position relative to fastener 200e, which adjustments may comprise translation along the Z axis (not indicated by an arrow in FIG. 4).

(15) The waveguide probe is alternatingly translated along the X and Y axes so that it follows a serpentine path to effect a raster scan of the area surrounding fastener 200e. Only the back and forth translations along the Y axis are indicated by arrows 420e in FIG. 4.

(16) The platform is translated along the X axis in a direction opposite to the first direction, as indicated by arrow 410f, until the waveguide probe is positioned in proximity to fastener 200f in the lower row.

(17) The position of the waveguide probe relative to the platform is adjusted to place the waveguide probe in a start scan position relative to fastener 200f, which adjustments may comprise translation along the Z axis (not indicated by an arrow in FIG. 4).

(18) The waveguide probe is alternatingly translated along the X and Y axes so that it follows a serpentine path to effect a raster scan of the area surrounding fastener 200f. Only the back and forth translations along the Y axis are indicated by arrows 420f in FIG. 4.

(19) The platform is translated in the direction opposite to the first direction, as indicated by arrow 410g, until the waveguide probe is positioned in proximity to the next fastener (not shown in FIG. 4) in the lower row.

FIG. 5 is a block diagram identifying components of a millimeter wave crack detection system in accordance with one embodiment. This system comprises a signal generator 512, an isolator 514, a signal divider 516 and first and second waveguides 602, 604. The signal generator 512 is configured to generate first and second millimeter wave signals which may have different frequencies. Millimeter waves may have a frequency from about 30 to about 300 GHz and a wavelength from about 1 to about 10 mm. The first and second millimeter wave signals are received by the signal divider 516, which passes the first signal to the first waveguide 602 and the second signal to the second waveguide 604. The isolator 514 is configured to reduce unwanted reflections from the signal divider 516 to the signal generator 512.

The wave signals emitted by the waveguides 602, 604 will be reflected by the metal structure, producing standing waves inside the waveguides. Still referring to FIG. 5, a characteristic (e.g., voltage) of the standing waves inside the waveguides 602, 604 is detected by respective diode detectors 522, 524. The detector outputs are collected by a data acquisition device 526 and sent to a signal analyzer 528. The signal analyzer 528 may be a processor programmed to identify a difference between the detector outputs and then determine whether an inconsistency (e.g., a crack) is present in the area around the fastener based on that difference.

Figure 6:
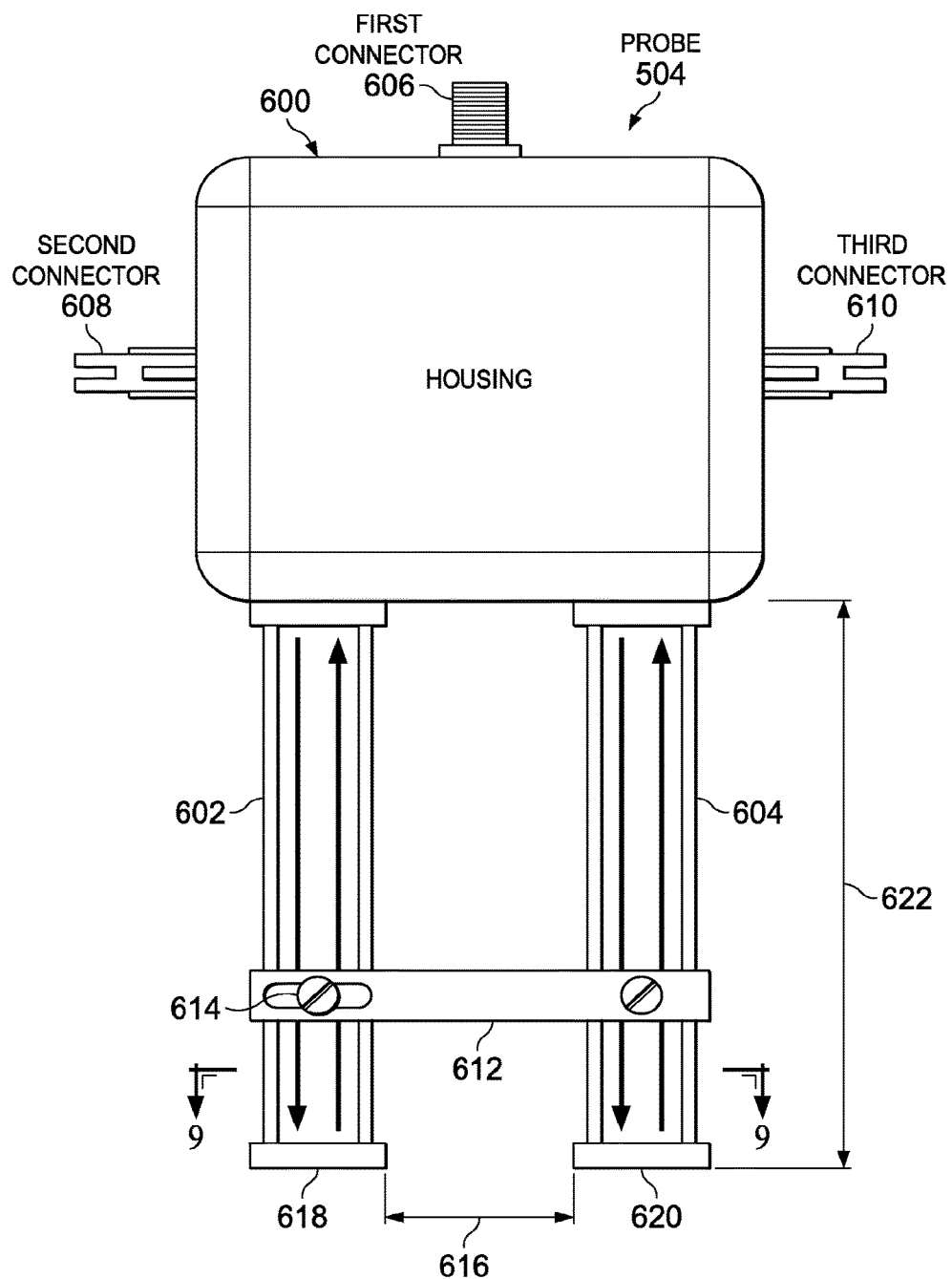
FIG. 6 is a diagram representing an elevation view of a waveguide probe suitable for mounting on a crawler vehicle.

The waveguide probe 504 depicted in FIG. 1 is shown on a magnified scale in FIG. 6. In this embodiment, the waveguide probe 504 comprises housing 600 to which first waveguide 602 and second waveguide 604 are adjustably connected. Waveguide probe 504 has a first connector 606, which is configured for connection to signal generator 512 shown in FIG. 5. Waveguide probe 504 also has a second connector 608 and a third connector 610. These two connectors are configured for connection to the data acquisition device 526 shown in FIG. 5.

Bar 612 is connected to the first and second waveguides 602, 604. Adjusting screw 614 may be used to secure the first waveguide 602 to bar 612 when the distance 616 between the first and second waveguides 602, 604 has been selected. Distance 616 may be selected such that the apertures (not shown) at the end 618 of the first waveguide 602 and the end 620 of the second waveguide 604 are disposed over opposite sides of a fastener. In this illustrative example, first waveguide 602 and second waveguide 604 have a length 622. In one implementation, length 622 may be about 2 inches. In other implementations, length 622 may be in a range from about 1 inch to about 4 inches.

Figure 7:
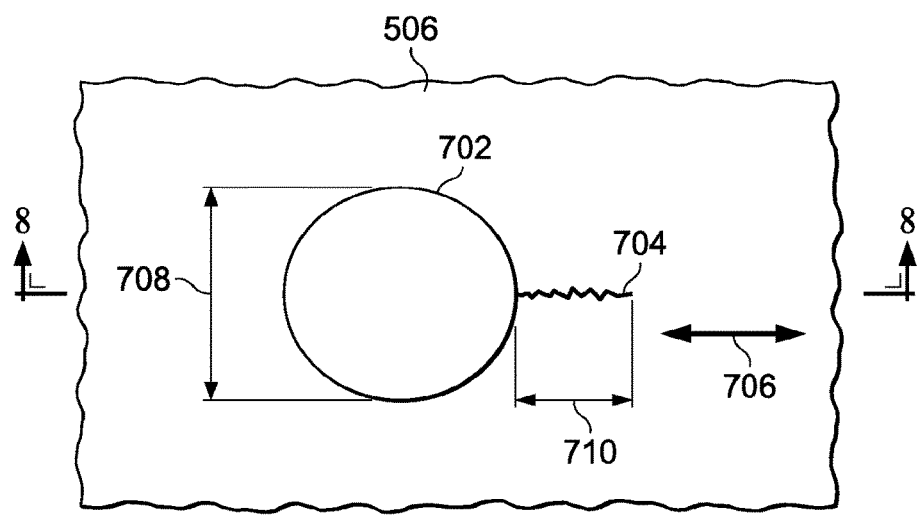
FIG. 7 is a diagram representing a plan view of a crack emanating from a fastener in a lap joint portion of a metallic skin.

FIG. 7 is a diagram representing a plan view of an inconsistency 704 emanating from a fastener 702 in a lap joint portion of a metallic fuselage skin 506. In this example, the inconsistency 704 is a crack extending in directions indicated by double-headed arrow 706 that is parallel to the row of fasteners to which fastener 702 belongs. Cracks typically extend in this direction due to the stresses and construction of an aircraft fuselage. In the scenario depicted in FIG. 7, the head of fastener 702 has diameter 708, while the inconsistency 704 has a length 710 measured at the surface of fuselage skin 506.

Figure 8:
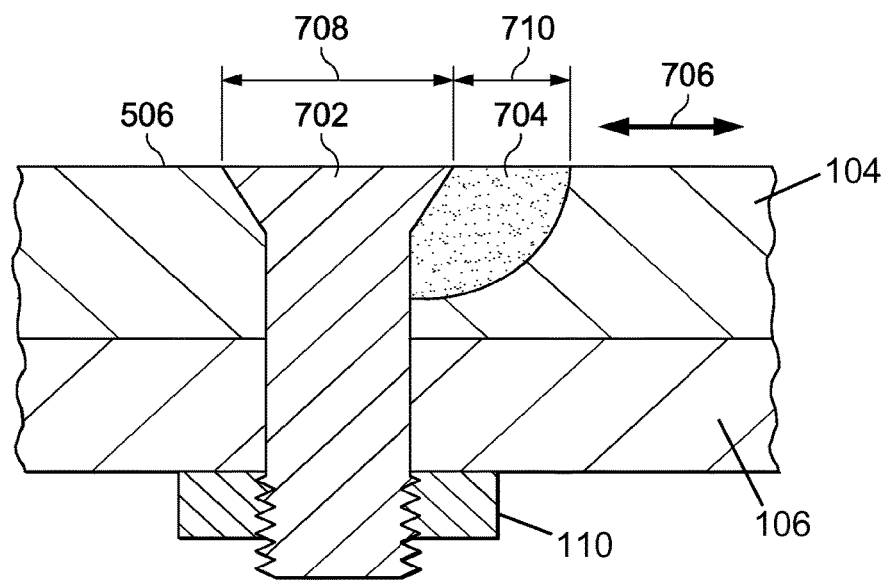
FIG. 8 is a diagram representing a sectional view of a crack emanating from a fastener in a lap joint portion of a metallic skin.

FIG. 8 is a diagram representing a sectional view of the inconsistency 704 emanating from the fastener 702. The fuselage skin 506 comprises overlapping metallic layers 104 and 106 which are fastened together by a multiplicity of fasteners. The fastener 702 is secured in aligned holes in layers 104, 106 by means of a nut 110.

Figure 9:
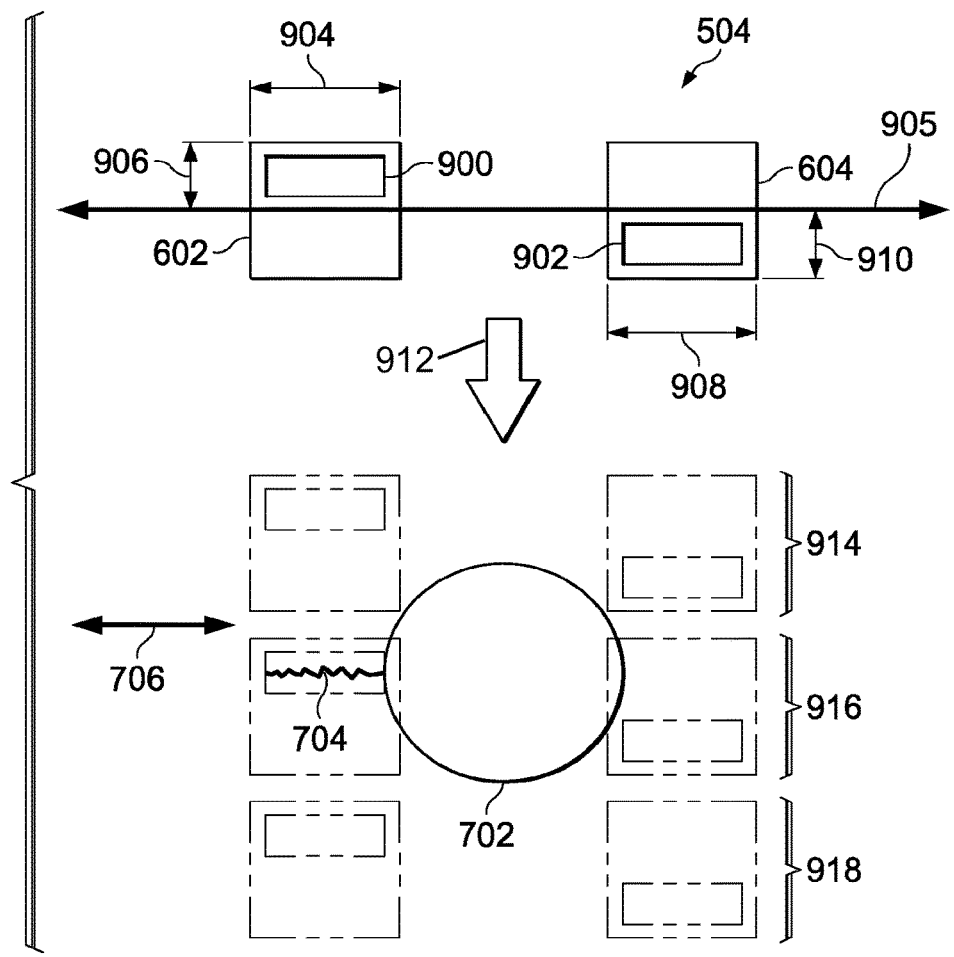
FIG. 9 is a diagram illustrating movement of an open-ended waveguide probe over a fastener in accordance with one embodiment.

FIG. 9 is a diagram illustrating movement of an open-ended waveguide probe 504 over a fastener 702 in accordance with one embodiment. FIG. 9 represents a cross-sectional view of waveguide probe 504 taken along lines 9-9 in FIG. 6. In the embodiment depicted in FIG. 9, the opening 900 in the first waveguide 602 is offset from the opening 902 in the second waveguide 604. This offset is with respect to line 905. This offset may reduce a possibility of signals and/or responses interfering with each other and indicating an inconsistency is absent in situations where inconsistencies are present on both sides of the fastener 702.

In this illustrative example, opening 900 has length 904 and width 906, and opening 902 has length 908 and width 910. In one implementation, the lengths 904 and 908 may be about 0.1 inch, and the widths 906 and 910 may be about 0.05 inch. The waveguides 602, 604 have respective rectangular cavities that extend upward from openings 900 and 902. However, other waveguide shapes may be used.

As illustrated in FIG. 9, the waveguide probe 504 may be moved in the direction of arrow 912 with respect to the fastener 702. The first waveguide 602 with opening 900 and the second waveguide 604 with opening 902 are shown in phantom in positions 914, 916, and 918. In this illustrative example, inconsistency 704 extends outward from the fastener 702.

Figure 10:
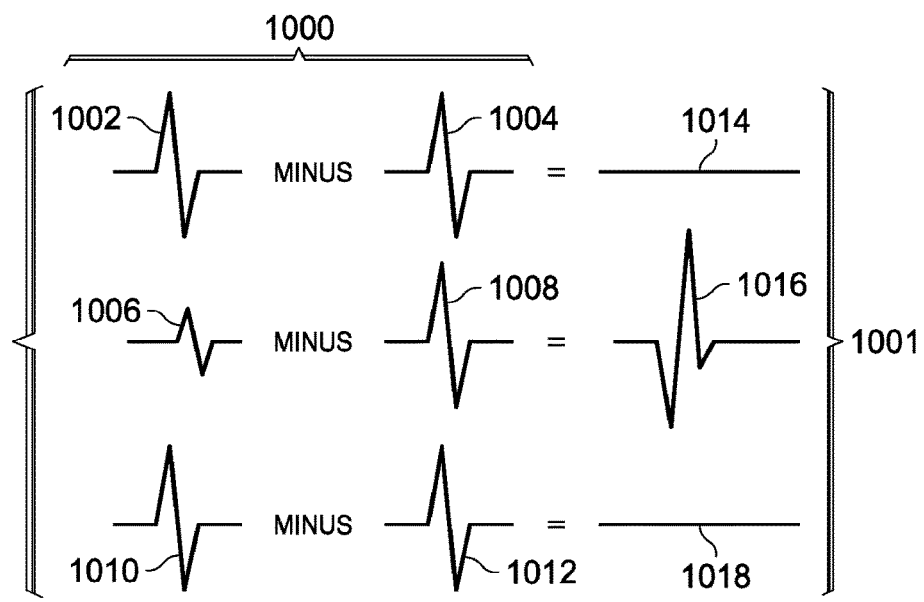
FIG. 10 is a diagram illustrating signals of a type that might be produced by a waveguide probe while scanning a fastener.

FIG. 10 is a diagram illustrating signals of a type that might be produced by the waveguide probe 504 while scanning the fastener 702 depicted in FIG. 9. The responses 1000 shown in FIG. 10 are examples of respective responses detected by first waveguide 602 and second waveguide 604 while in positions 914, 916, and 918 shown in FIG. 9. In this illustrative example, response 1002 is detected by first waveguide 602, and response 1004 is detected by second waveguide 604 in position 914; response 1006 is detected by first waveguide 602, and response 1008 is detected by second waveguide 604 in position 916; and response 1010 is detected by first waveguide 602 and response 1012 is detected by second waveguide 604 in position 918.

The difference signals 1001 shown in FIG. 10 represent the differences between the respective responses detected by the first and second waveguides. Difference signal 1014 represents a substantially zero difference between response 1002 and response 1004. Accordingly, difference signal 1014 indicates the absence of an inconsistency at position 914. Difference signal 1016 represents the non-zero difference between response 1006 and response 1008. Difference signal 1016 indicates that inconsistency 704 was detected when waveguide probe 504 was at position 916. Difference signal 1018 represents a substantially zero difference between response 1010 and response 1012. Accordingly, the difference signal 1018 indicates the absence of an inconsistency at position 918.

Thus, as waveguide probe 504 is moved relative to fastener 702, an inconsistency on either side may produce a detectable difference in the responses detected by the first and second waveguides. These differences may be measured in terms of amplitude, phase, or a combination of the two. The offset in the openings may reduce the likelihood that a difference of zero will be produced if respective inconsistencies having similar size and orientation are present on both sides of the fastener.

Figure 11:
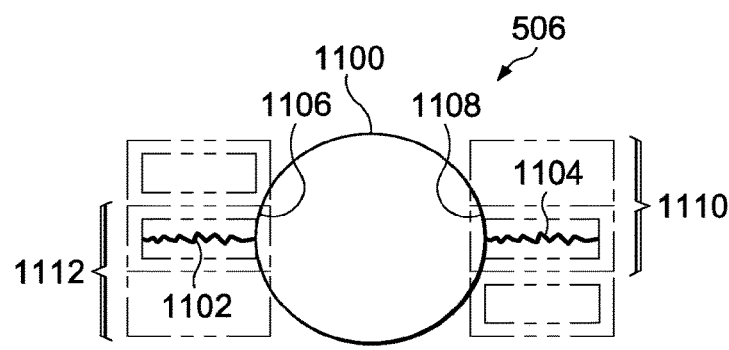
FIG. 11 is a diagram illustrating scanning of a structure having two cracks emanating from a fastener.

FIG. 11 is a diagram illustrating scanning of a portion of a metallic fuselage skin 506 having two inconsistencies 1102 and 1104 emanating from respective sides 1106 and 1108 of a fastener 1100. For the purpose of illustration, it will be assumed that inconsistencies 1102 and 1104 have similar dimensions and orientations. In this illustrative example, the offset between the openings of the waveguides may prevent responses from indicating the absence of an inconsistency when the response signals from the respective inconsistencies 1102 and 1104 produce a difference signal less than the specified threshold. As can be seen in FIG. 11, when the waveguide probe is in position 1110, inconsistency 1104 can be detected. Later, when the waveguide probe moves to position 1112, inconsistency 1102 can be identified.

The illustration of waveguide probe 504 and inconsistencies on a metallic skin panel in FIGS. 5-11 are not meant to imply physical or architectural limitations to the manner in which waveguide probe 504 may be implemented. Further, the manner in which waveguide probe 504 may be moved with respect to metallic skin 506 may be performed in ways other than what is shown. For example, waveguide probe 504 may be rotated around each fastener, rather than moved in the direction of arrow 706.

Figure 12:
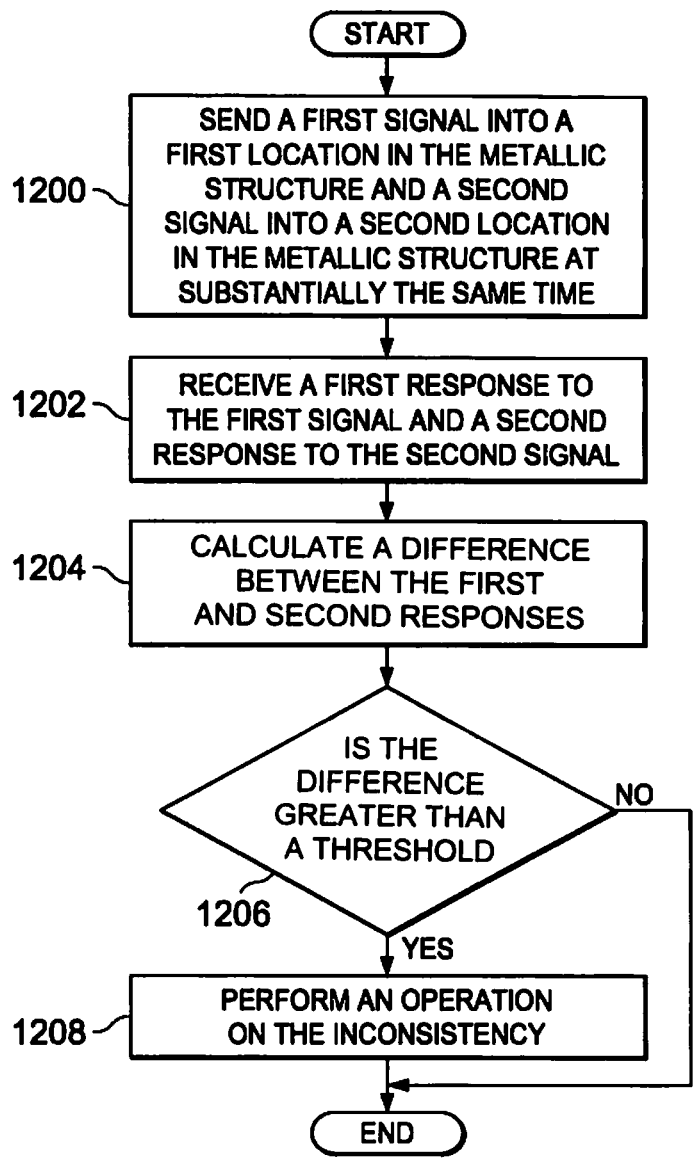
FIG. 12 is a flowchart identifying steps of a process for inspecting a structure in accordance with one embodiment.

FIG. 12 is a flowchart identifying steps of a process for inspecting a structure in accordance with one embodiment. This process may be implemented in an inspection environment and using the equipment depicted in FIG. 1. The process begins by sending a first signal into a first location in the metallic structure and a second signal into a second location in the metallic structure at substantially the same time (operation 1200). The process receives a first response to the first signal and a second response to the second signal (operation 1202). The first response is compared to the second response and a difference between the first and second responses is calculated (operation 1204). A determination is made as to whether the difference is greater than a pre-selected threshold value considered to be indicative of the presence of an inconsistency (operation 1206). If the difference is not greater than the pre-selected threshold value (i.e., an inconsistency is not present), the process terminates. Otherwise, an operation is performed on the inconsistency (operation 1208). The operation may be, for example, a rework operation. The rework operation may include reworking the metallic structure to reduce or remove the inconsistency or replacing the metallic structure. The process terminates thereafter.

Figure 13:
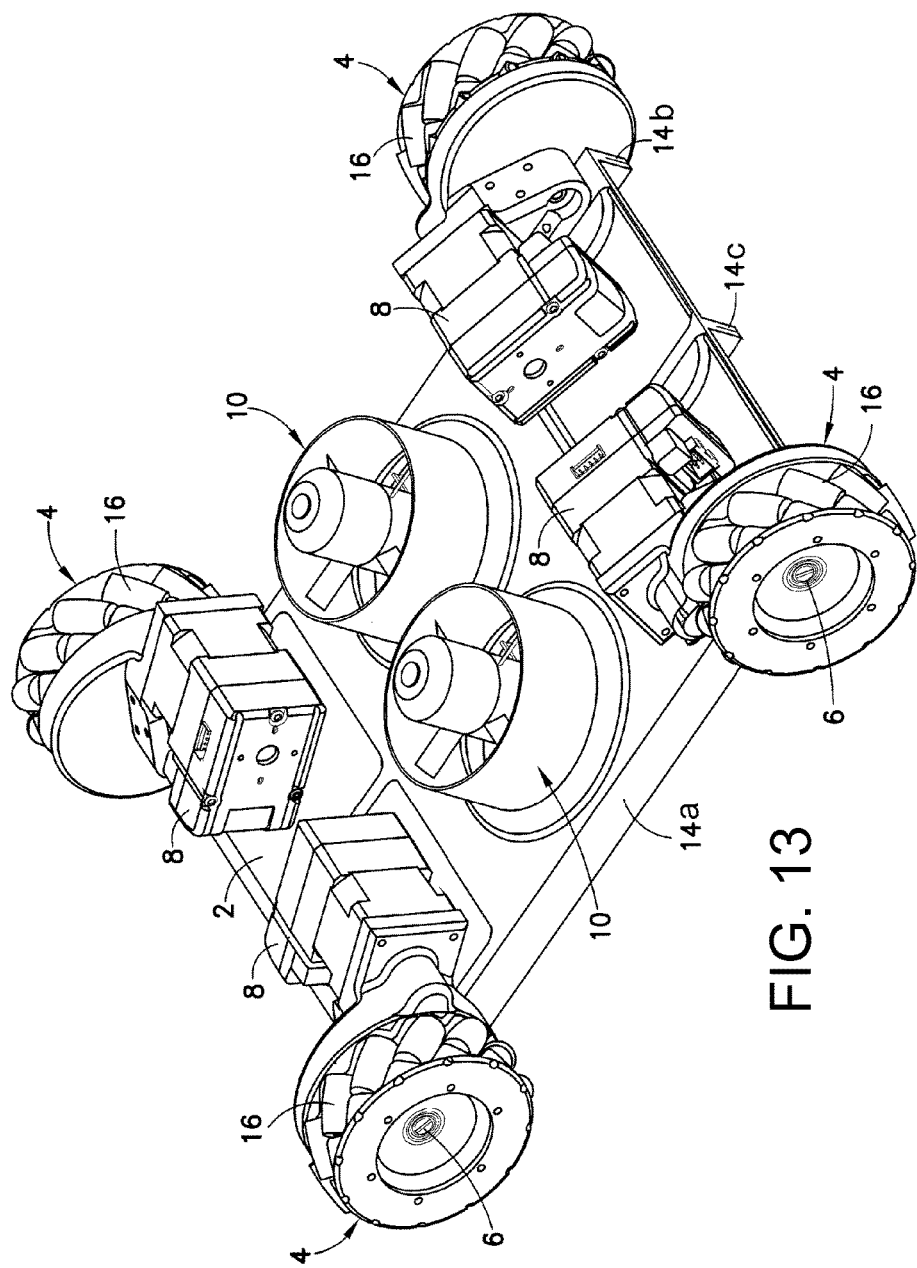
FIG. 13 is a diagram representing an isometric view of parts of a holonomic-motion crawler vehicle that could be adapted to carry a multi-motion inspection head. The connections for supplying electrical power and signals for controlling vehicle motion are not shown.

FIG. 13 is a diagram representing an isometric view of parts of a holonomic-motion crawler vehicle that could be adapted to carry a multi-motion inspection head. More specifically, crawler vehicle 120 depicted in FIG. 1 could be a holonomic-motion vehicle. A holonomic motion system is one that is not subject to motion constraints. This type of system can translate in any direction while simultaneously rotating or rotate without translation.

FIG. 13 shows parts of a holonomic-motion crawler vehicle having four Mecanum wheels and two suction zones in accordance with one embodiment. The electrical connections for supplying signals for controlling operation of the depicted components are not shown in FIG. 13. This holonomic-motion crawler vehicle comprises a frame 2 with four Mecanum wheels 4 (two type "A" and two type "B") mounted to the frame 2 by means of respective axles 6, and further comprises four independently controlled stepper motors 8 (one per wheel). The Mecanum wheels 4 are arranged with the "A" pair on one diagonal and the "B" pair on the other, with each having its axle 6 perpendicular to a line running through the center of the vehicle. Each stepper motor 8 controls the rotation of a respective wheel 4.

The embodiment depicted in FIG. 13 also has two suction devices 10 arranged side by side in the middle of the frame 2, midway between the front and rear wheels. In this particular embodiment, each suction device is a respective electric ducted fan (EDF) 10 which is mounted in a respective opening (not shown in FIG. 13) formed in the frame 2. Each electric ducted fan 10 comprises a fan which is rotatable about an axis, a duct surrounding the fan, and an electric motor which drives the fan to rotate in a direction such that air is propelled from a respective channel or space underneath the frame (hereinafter "suction zone") up through the fan duct, thereby creating suction in the corresponding suction zone. The two suction zones are bounded on opposing sides by longitudinal low-surface-friction flexible skirts 14a-14c which are attached to the frame 2, the middle skirt 14c forming a common boundary wall separating the two suction zones. The skirts 14a-14c may extend downward so that their bottom edges contact the surface on which the vehicle is moving.

Although not shown in FIG. 13, the crawler vehicle can be tethered to a support system by a cable which supplies electrical power to the stepper motors 8 and electric ducted fans 10 on the vehicle. The cable also provides control signals from a controller (e.g., a computer) which controls the operation of the stepper motors 8 and electric ducted fans 10. The crawler vehicle further comprises a converter box (not shown) mounted to the frame 2. The converter box converts USB signals from the controller (not shown) into pulse-width-modulated signals for controlling the electric ducted fan motors.

In accordance with an alternative embodiment, the crawler vehicle could be battery-powered, instead of receiving electrical power via the tether cable. Also the motor controller could be a microprocessor or microcomputer mounted onboard the crawler vehicle, rather than using a ground-based computer to control the vehicle by means of controls signals carried by a tether cable. Alternatively, the motors onboard the crawler vehicle can be controlled via a wireless connection to an off-board controller.

The crawler vehicle shown in FIG. 13 utilizes four Mecanum wheels. Each Mecanum wheel 4 has a multiplicity of tapered rollers 16 rotatably mounted to its circumference, each roller being freely rotatable about its axis. These rollers typically have an axis of rotation which lies at a 45° angle with respect to the plane of the wheel. Type "A" Mecanum wheels have left-handed rollers, while Type "B" Mecanum wheels have right-handed rollers. The vehicle can be made to move in any direction and turn by varying the speed and direction of rotation of each wheel.

Figure 14:
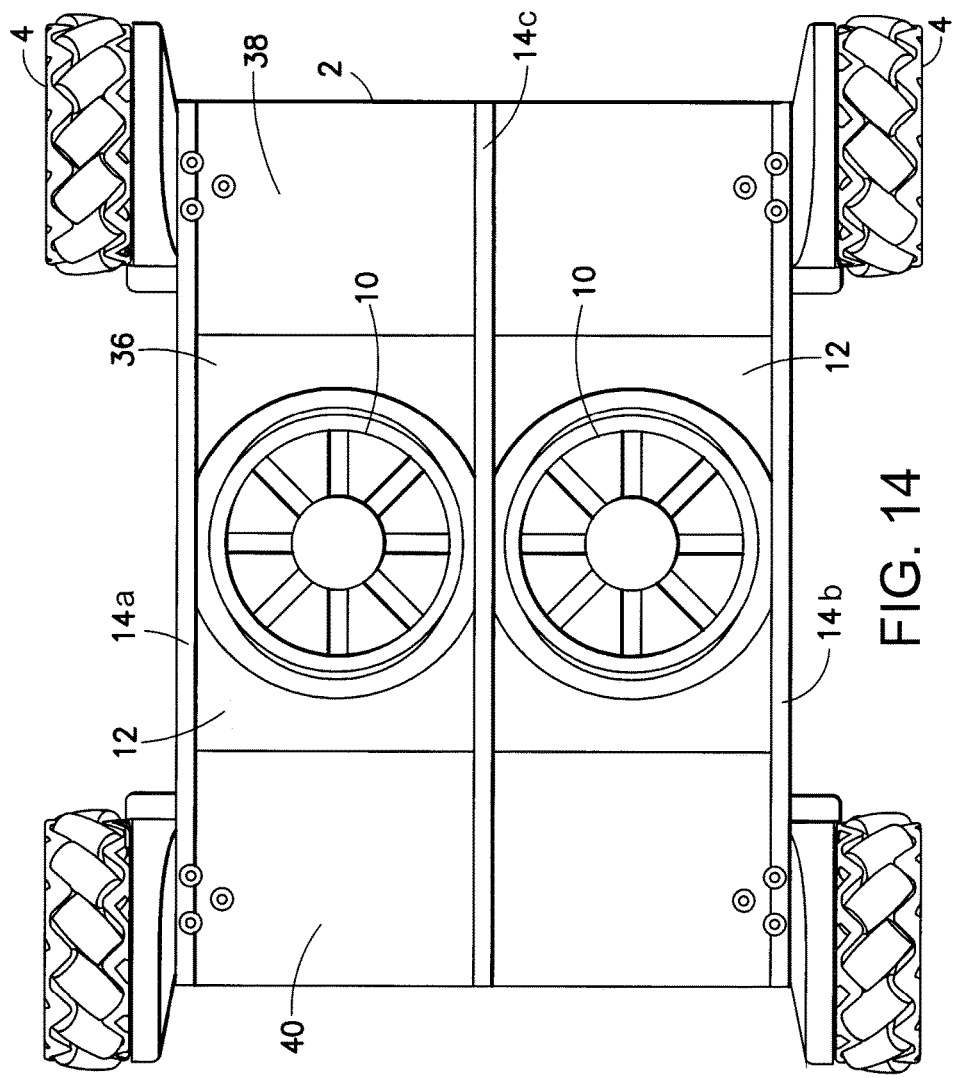
FIG. 14 is a diagram representing a bottom view of a Mecanum-wheeled crawler vehicle having dual suction zones.

FIG. 14 is a diagram showing a bottom view of a Mecanum-wheeled crawler vehicle having dual suction zones 12 separated by a common skirt 14c which bisects the bottom surface of the frame along a longitudinal axis. In this particular construction, the upper half of the bottom surface between the uppermost skirt 14a and the common skirt 14c comprises a flat central surface 36 having an opening in which the fan of the electric ducted fan is installed. This flat central surface 36 is flanked by forward and rearward convex surface 38 and 40. Each convex surface 38 and 40 may be an aerodynamically streamlined surface which forms a respective throat with opposing portions of the surface on which the vehicle is moving. Thus, the contoured bottom surface of the frame, the skirts and the surface on which the vehicle is moving define respective channels that allow sufficient air to be sucked up through the corresponding electric ducted fan to generate a desired suction force. The portion of each channel between the lowest points of the convex surfaces 38 and 40 forms a respective suction zone 12. In the particular embodiment depicted in FIG. 14, the suction zones are separated by the common skirt 14c and are in fluid communication with the respective openings in which the ducted fans are installed. These openings may be substantially conical along a lowermost portion thereof to facilitate the flow of air out the suction zone.

It should be appreciated that the under-body surface shape seen in FIG. 14 is an exemplary implementation. The under-body surface may have many different shapes conducive to the flow of air from the front and rear of the vehicle through the space underneath the vehicle and then up through the ducts of the electric ducted fans 10.

The system disclosed herein combines the directional control advantages of a Mecanum-wheeled crawler vehicle with the ability to work on inclined, vertical or inverted surfaces. As compared to inspection systems that attach to the inspection surface, or systems that use a large robotic manipulator arm, a crawler vehicle has more flexibility in the types of regions that can be inspected, and is safer for operators and the object being inspected. The main advantage that the system disclosed herein has over other systems is the combination of the ability to hold the vehicle's position on any surface without sliding (due to the controlled suction system) and the ability to move in any direction (due to the holonomic-motion platform). With a holonomic-motion system that can move on level, inclined and vertical surfaces (and potentially inverted surfaces), general-purpose motion control is enabled for millimeter wave crack detection.

Figure 15:
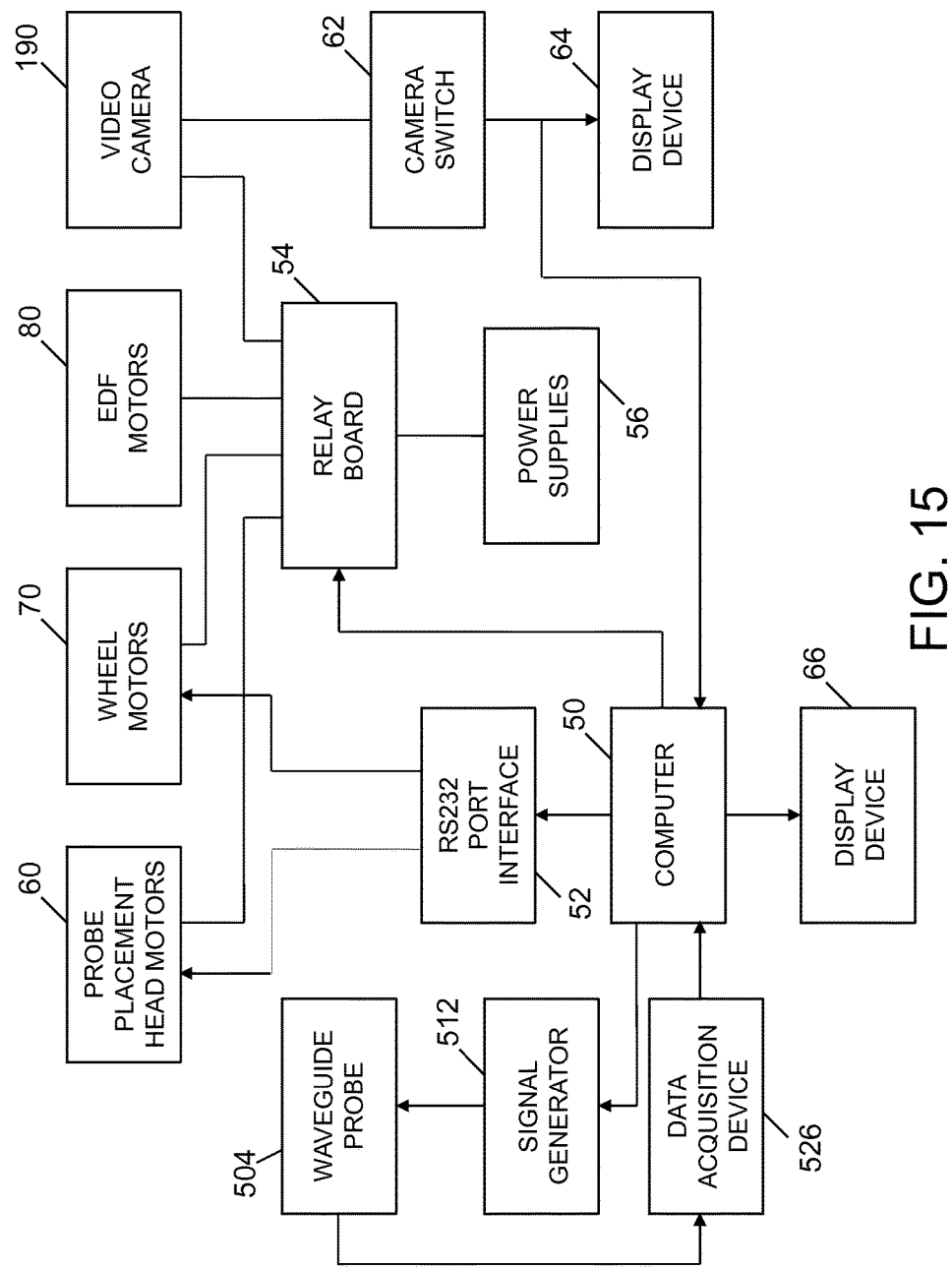
FIG. 15 is a block diagram identifying components of a system for non-destructive inspection of metal around a fastener in accordance with one embodiment.

FIG. 15 is a block diagram identifying components of an automated system for non-destructive inspection of metal around a fastener in accordance with an embodiment wherein the platform is a holonomic-motion crawler vehicle equipped with a multi-stage probe placement head that supports a rotatable millimeter waveguide probe. The probe placement head supports a plurality of motors 60, three of which drive translation of the waveguide probe 504 along X, Y and Z axes respectively and one of which drives rotation of the waveguide probe 504 about the Z axis. The holonomic-motion crawler vehicle depicted in FIGS. 13 and 14 carries four wheel motors 70, which respectively drive rotation of four Mecanum wheels, and two EDF motors 80 which drive rotation of two electric ducted fans. All of the motors 60, 70 and 80 received electrical power from power supplies 56 via switches on a relay board 54. The states of those switches are controlled by a computer 50. More specifically, the closure of a switch on relay board 54 is activated by a signal received from computer 50 via a serial (e.g., RS-232) port interface 52. The computer 50 may comprise a general-purpose computer programmed with motion control application software comprising respective software modules for controlling the various stepper motors. The computer 50 outputs control signals to probe placement head motors 60 and wheel motors 70 via the same serial port interface 52 to selectively activate/deactivate each motor. When activated, the stepper motors are programmed to execute respective motion control functions in accordance with selections made by the system operator using an interactive control interface (not shown).

The holonomic-motion crawler vehicle may be equipped with a video camera 190 that captures a live view of the volume of space below the probe placement head. The video camera 190 receives power from a power supply in response to activation of a switch that is part of relay board 54 and activated by computer 50 via serial port interface 52. Imaging data from video camera 190 is received by a display monitor 64 via a camera switch 62. The imaging data is also sent to the computer 50 for image processing, e.g., using pattern recognition software.

The computer 50 may also be programmed to control the signal generator 512 to generate millimeter wave signals inside the waveguide probe 504. The detector outputs from the waveguide probe 504 are collected by a data acquisition device 526 and sent to computer 50, which is further programmed with signal analyzing software. The signal analyzing software can identify a difference between the detector outputs and then determine whether an inconsistency (e.g., a crack) is present in the area being inspected.

In accordance with one embodiment of the system depicted in FIG. 1, probe placement head 100 comprises: a Z-axis stage 140 that is displaceable along a Z axis relative to the block assembly 130; an X-axis stage 150 that is displaceable along an X axis relative to the Z-axis stage 140; and a Y-axis stage 160 that is displaceable along a Y axis relative to the X-axis stage 150. The X-, Y- and Z-axis stages may be translatably coupled by means of respective linear-motion bearings. These translatable stages may be mechanically coupled to respective stepper motors (see probe placement head motors 60 in FIG. 15) by any suitable drive mechanism known in the art. For example, each stage could have a respective attached nut which threadably engages a respective lead screw which is driven to rotate by a respective stepper motor, thereby converting the rotation of the motor output shaft into translation of the stage.

In accordance with some alternative embodiments, the apparatus may comprise a multi-stage probe placement head comprising a block assembly, a first stage translatably coupled to the block assembly, and a second stage translatably coupled to the first stage; a mandrel rotatably coupled to the second stage of the multi-stage probe placement head; and a millimeter waveguide probe attached to the mandrel. For example, if the multi-stage probe placement head is mounted on a crawler vehicle, robotic arm or scanning bridge that can be positioned with sufficient precision along a X axis which is parallel to a row of fasteners, then a two-stage probe placement head could be provided which has a Y-axis stage and a Z-axis stage, both of which are controllable to enable precise positioning in the Y and Z directions. Accordingly, probe placements heads within the scope of the teachings herein may have only two translating stages in some applications.

In accordance with other alternative embodiments, an eddy current probe mounted in front of the waveguide probe may be used to locate a fastener (instead of relying on camera images). The eddy current probe can center electrically on a fastener. Since the position of the eddy current probe in the frame of reference of the platform is known, the position of the fastener in that same frame of reference could be determined from the eddy current probe output. The waveguide probe could then be positioned to align with that fastener.

While apparatus and methods for inspecting metal around fasteners have been described with reference to various embodiments, it will be understood by those skilled in the art that various changes may be made and equivalents may be substituted for elements thereof without departing from the scope of the teachings herein. In addition, many modifications may be made to adapt the concepts and reductions to practice disclosed herein to a particular situation. Accordingly, it is intended that the subject matter covered by the claims not be limited to the disclosed embodiments.

As used in the claims, the term "computer system" should be construed broadly to encompass a system having at least one computer or processor, and which may have multiple computers or processors that communicate through a network or bus. As used in the preceding sentence, the terms "computer" and "processor" both refer to devices comprising a processing unit (e.g., a central processing unit, an integrated circuit or an arithmetic logic unit) capable of executing instructions.

In one or more of the applications disclosed herein, a first program comprises instructions for processing imaging data using pattern recognition; a second program comprises instructions for controlling a motorized multi-stage probe placement head, a third program comprises instructions for controlling a millimeter waveguide probe, and a fourth program comprises instructions for analyzing signals received from the millimeter waveguide probe.

The method claims set forth hereinafter should not be construed to require that the steps recited therein be performed in alphabetical order (any alphabetical ordering in the claims is used solely for the purpose of referencing previously recited steps) or in the order in which they are recited. Nor should they be construed to exclude any portions of two or more steps being performed concurrently or alternatingly. For example, translation of two or more stages may occur concurrently or sequentially or may partially overlap in time.

The invention claimed is:

1. A system for non-destructive inspection of metal around a fastener, comprising:
    a crawler vehicle comprising a frame, a plurality of wheels rotatably coupled to said frame and a first plurality of motors respectively mechanically coupled to said plurality of wheels;
    a multi-stage probe placement head mounted to said frame, said multi-stage probe placement head comprising an X-axis stage, a Y-axis stage and a Z-axis stage, said X-, Y- and Z-axis stages being respectively translatable in X, Y and Z directions;
    a second plurality of motors respectively mechanically coupled for driving translation of said X-, Y- and Z-axis stages;
    a waveguide probe rotatably coupled to said third stage of said multi-stage probe placement head, said waveguide probe being rotatable about the Z axis;
    a motor mechanically coupled for driving rotation of said waveguide probe about the Z axis;
    a camera mounted to said frame, said camera being directed toward a volume of space under said multi-stage probe placement head; and
    a computer system programmed to perform the following operations:

processing imaging data acquired by the camera;
controlling said motors; and
controlling said waveguide probe to transmit wave signals.

2. The system as recited in claim 1, wherein said crawler vehicle further comprises at least one suction device.

3. The system as recited in claim 1, wherein said operation of processing imaging data acquired by said camera comprises recognizing imaging data representing an image of a fastener and then determining a position of said fastener in a frame of reference of said platform.

4. The system as recited in claim 3, wherein said operation of controlling said motors comprises activating and later de-activating at least one of said second plurality of motors to cause said waveguide probe to be moved to a start position at which a center axis of said waveguide probe intersects said fastener, and activating said motor mechanically coupled for driving rotation of said waveguide probe about the Z axis while said waveguide probe is in said start position, and said operation of controlling said waveguide probe to transmit wave signals comprises activating said waveguide probe to transmit wave signals while said waveguide probe is rotating.

5. The system as recited in claim 3, wherein said operation of controlling said motors comprises activating and later de-activating at least one of said second plurality of motors to cause said waveguide probe to be moved to a start position at which a central axis of said waveguide probe is not coaxial with a central axis of said fastener.

6. The system as recited in claim 5, wherein said operation of controlling said motors further comprises activating and later de-activating said motor of said second plurality of motors which is mechanically coupled for driving translation of said Y-axis stage to cause said waveguide probe to translate in a Y direction from said start position to a stop position, and said operation of controlling said waveguide probe to transmit wave signals comprises activating said waveguide probe to transmit wave signals while said waveguide probe is moving from said start position to said stop position.

7. The system as recited in claim 1, wherein said suction device comprises a fan rotatably coupled to said frame and a motor mounted to said frame and mechanically coupled to said suction device for driving rotation of said fan.

* * * * *